US007012128B2

(12) United States Patent
Bernards et al.

(10) Patent No.: US 7,012,128 B2
(45) Date of Patent: Mar. 14, 2006

(54) INTERACTION BETWEEN CYCLIN D1 AND STEROID RECEPTOR CO-ACTIVATORS AND USES THEREOF IN ASSAYS

(75) Inventors: René Bernards, Alconde (NL); Renate Zwijsen, Utrecht (NL)

(73) Assignee: TopoTarget UK Limited, Abingdon (GB)

( * ) Notice: Subject to any disclaimer, the term of this patent is extended or adjusted under 35 U.S.C. 154(b) by 454 days.

(21) Appl. No.: 09/953,031

(22) Filed: Sep. 14, 2001

(65) Prior Publication Data

US 2002/0177177 A1 Nov. 28, 2002

Related U.S. Application Data

(63) Continuation of application No. 09/302,305, filed on Apr. 30, 1999, now Pat. No. 6,350,572, which is a continuation of application No. PCT/GB99/00440, filed on Feb. 12, 1999.

(30) Foreign Application Priority Data

Feb. 12, 1998 (GB) ............................................. 9803035
Aug. 20, 1998 (GB) ............................................. 9818243

(51) Int. Cl.
A61K 38/00 (2006.01)
C07K 2/00 (2006.01)
C07K 4/00 (2006.01)
C07K 5/00 (2006.01)
C07K 7/00 (2006.01)

(52) U.S. Cl. ............................. 530/300; 514/1; 514/2; 514/8; 514/14

(58) Field of Classification Search ................. 530/300, 530/390; 514/1, 2, 8, 14

See application file for complete search history.

(56) References Cited

U.S. PATENT DOCUMENTS 6,350,572 B1 2/2002 Bernards et al.

FOREIGN PATENT DOCUMENTS

WO 97/40378 10/1997

OTHER PUBLICATIONS

Zwijsen et al. Ligand–independent recruitment of steroid receptor coactivators to estrogen receptor by cyclin D1. Genes and Development 12(22):3488–3498, 1998.
Allen, *Biopharm. Drug Dispos.*, 11(6):477–498 (1990).
Andersen, et al., *EMBO J.*, 16:958–967 (1997).
Anzick, et al., *Science*, 277:965–968 (1997).
Baldetorp, et al., *Cytometry*, 33(4):385–393 (1998).
Baniahmad. et al., *Proc. Natl. Acad. Sci. USA*. 90:8832–8836 (1993).
Beato, *Cell*, 56:335–344 (1989).

Beijersbergen and Bernards, *Biochem. Biophys. Acta. Reviews on Cancer*, 1287:103–120 (1996).
Brzozowski, et al., *Nature*, 389:753–758 (1997).
Buckley, et al., *Oncogene*, 8:2127–2133 (1993).
Cavailles, et al., *Proc. Natl. Acad. Sci. USA*, 91:10009–10023 (1994).
Chakravarti, et al., *Nature*, 383:99–103 (1996).
Chen, et al., *Cell*, 90:569–580 (1997).
Danielian. et al., *EMBO J.*, 11:1025–1033 (1992).
Derossi, et al., *J. Biol. Chem.*, 269:10444–10450 (1994).
Elliot and O'Hare, *Cell*, 88:223–233 (1997).
Evans, *Science*, 240:889–895 (1988).
Fantl, et al., *Genes & Development*, 9:2364–2372 (1995).
Fawell. et al., *Proc. Natl. Acad. Sci. USA*, 91:664–668 (1994).
Fields and Song, *Nature*, 340:245–246 (1989).
Fuqua, et al., *J. Cell. Biochem.*, 51:135–139 (1993).
Gillett, et al., *Int. J. Cancer*, 69:92–99 (1996).
Gillett. et al., *Cancer Res.*, 54:1812–1817 (1994).
Guo, et al., *J. Biol. Chem.*, 270:27562–27568 (1995).
Hanstein, et al., *Proc. Natl. Acad. Sci. USA*, 93:11540–11545 (1996).
Heery, et al., *Nature*, 387:733–736 (1997).
Hong, et al., *Mol. Cell. Biol.*, 17:2735–2744 (1997).
Ing, et al., *J. Biol. Chem.*, 267:17617–17623 (1992).
Jacq, et al., *Cell.* 79:107–117 (1994).
Jeffrey, et al., *Nature*. 376:313–320 (1995).
Jenster, et al., *Proc. Natl. Acad. Sci. USA*, 94:7879–7884 (1997).
Kalkhoven, et al., *EMBO J.*, 17:232–243 (1998).
Kamei, et al., *Cell*, 85:403–414 (1996).
Kumar, et al., *Cell*, 51:941–951 (1987).
Kumar and Chambon, *Cell*, 55:145–156 (1988).
Le Douarin et al., *EMBO J.*, 15:6701–6715 (1996).
Le Douarin, et al., *EMBO J.*, 14:2020–2033 (1995).
Li, et al., *Proc. Natl. Acad. Sci. USA*. 94:8479–8484 (1997).
McGuire, et al., *Mol. Endocrinol.*, 5:1571–1577 (1991).
Miksicek, et al., *Semin. Cancer Biol.*, 5:369–379 (1995).
Mitchell and Tjian, *Science*, 245:371–388 (1989).
Musgrove, et al., *Proc. Natl. Acad. Sci. USA*, 91:8022–8026 (1994).
Neuman, et al., *Mol. Cell. Biol.*, 17:5338–5347 (1997).
Ogata, et al., *Immunol. Methods.* 148(1–2)i:15–22 (1992).
Ogryzko, et al., *Cell*, 87:953–959 (1996).
Onate, *Science*, 270:1354–1357 (1995).

(Continued)

Primary Examiner—Alana M. Harris
(74) Attorney, Agent, or Firm—Nixon & Vanderhye P.C.

(57) ABSTRACT

The present invention relates to the finding that cyclin D1 interacts in a ligand-independent fashion with coactivators of the SRC-1 family. The direct interaction of cyclin D1 enhances estrogen receptor (ER) mediated transcription and provides a novel target for the development of assays for substances which modulate the cell cycle. The invention provides assay methods for the prevention of growth of tumors, for assays for compounds useful in the prevention of tumors and compounds obtainable by such assays.

5 Claims, 11 Drawing Sheets

OTHER PUBLICATIONS

Figure 2A:
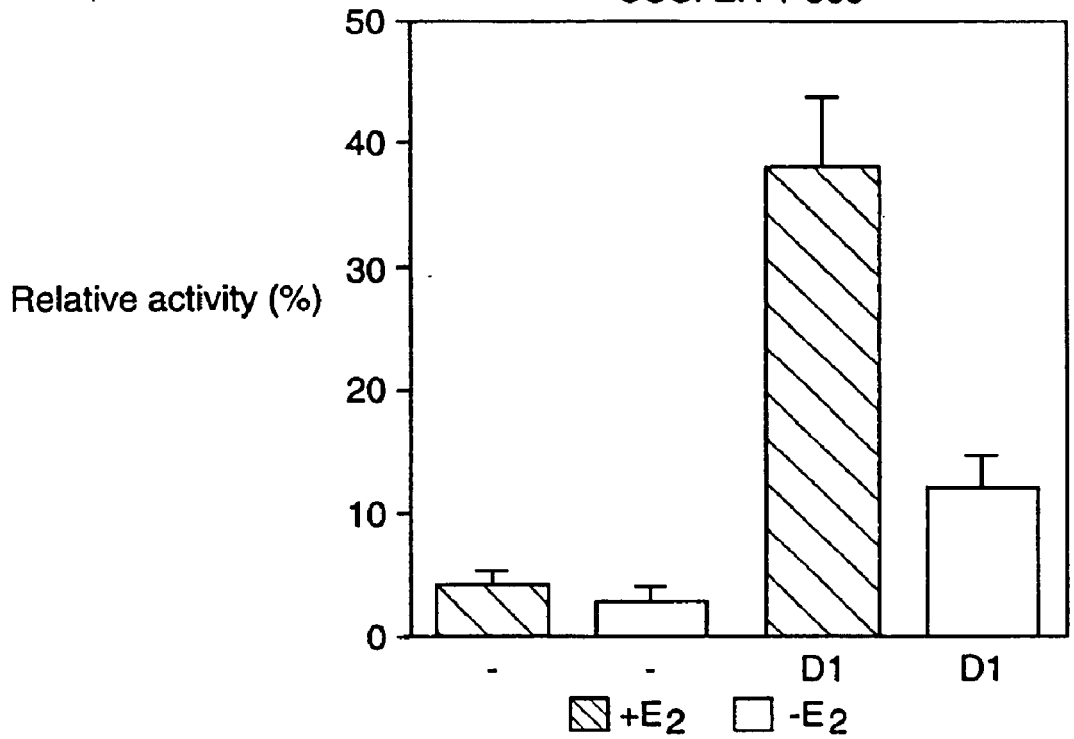

Pugh and Tjian, *Cell*, 61:1187–1197 (1990).
Renaud, et al., *Nature*, 378:681–689 (1995).
Rost and Sander, *J. Mol. Biol.*, 232:584–599 (1993).
Sadovsky, et al., *Mol. Cell. Biol.*, 1:1554–1563 (1995).
Schuuring, et al., *Oncogene*, 7:355–361 (1992).
Schuuring, et al., *Cancer Res.*, 52–5229–5234 (1995).
Sicinski, et al., *Cell*, 82:621–630 (1995).
Smith, et al., *Proc. Natl. Acad. Sci. USA*, 93:8884–8888 (1996).
Spencer, et al., *Nature*, 389:194–198 (1997).
Torchia, et al., *Nature*, 387–677–684 (1997).
Tzukerman, et al., *Mol. Endocrinol.*, 8:21–30 (1994).
van Diest, et al., *Am. J. Pathol.*, 150:705–711 (1997).
Vogel, et al., *EMBO J.*, 15:3667–3675 (1996).
vom Baur, et al., *EMBO J.*, 15:110–124 (1996).
Wang, et al., *Nature*, 369:669–671 (1994).
White, et al., *EMBO J.*, 16:1427–1435 (1997).
Xiong, et al., *Cell*, 65:691–699 (1991).
Xiong, et al., *Genomics*, 13:575–584 (1992).
Yao, et al., *Proc. Natl. Acad. Sci. USA*, 93:10626–10631 (1996).
Zwijsen, et al., *Mol. Cell. Biol.*, 16:2554–2560 (1996).
Zwigsen, et al., *Cell*. 88:405–415 (1997).

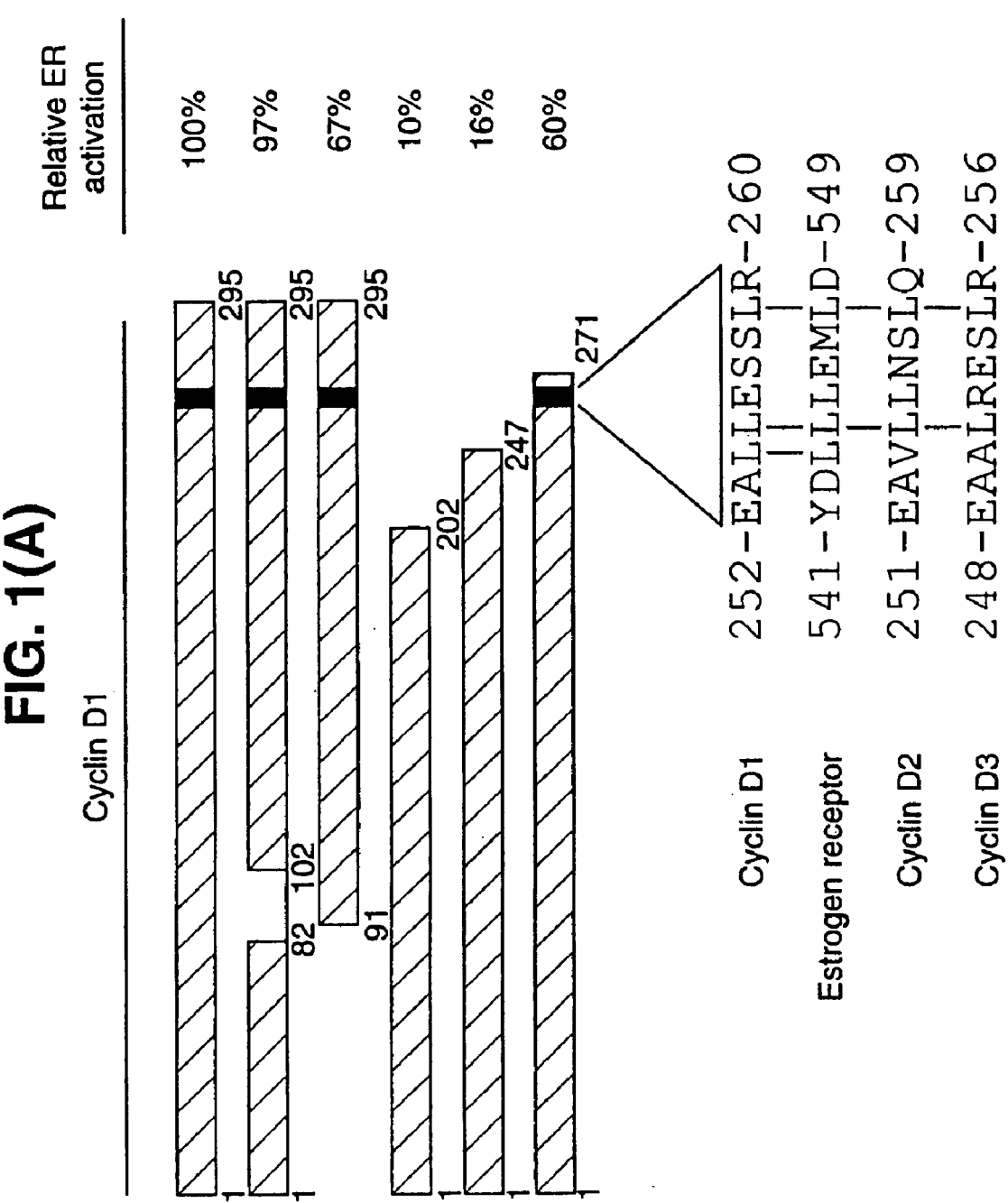

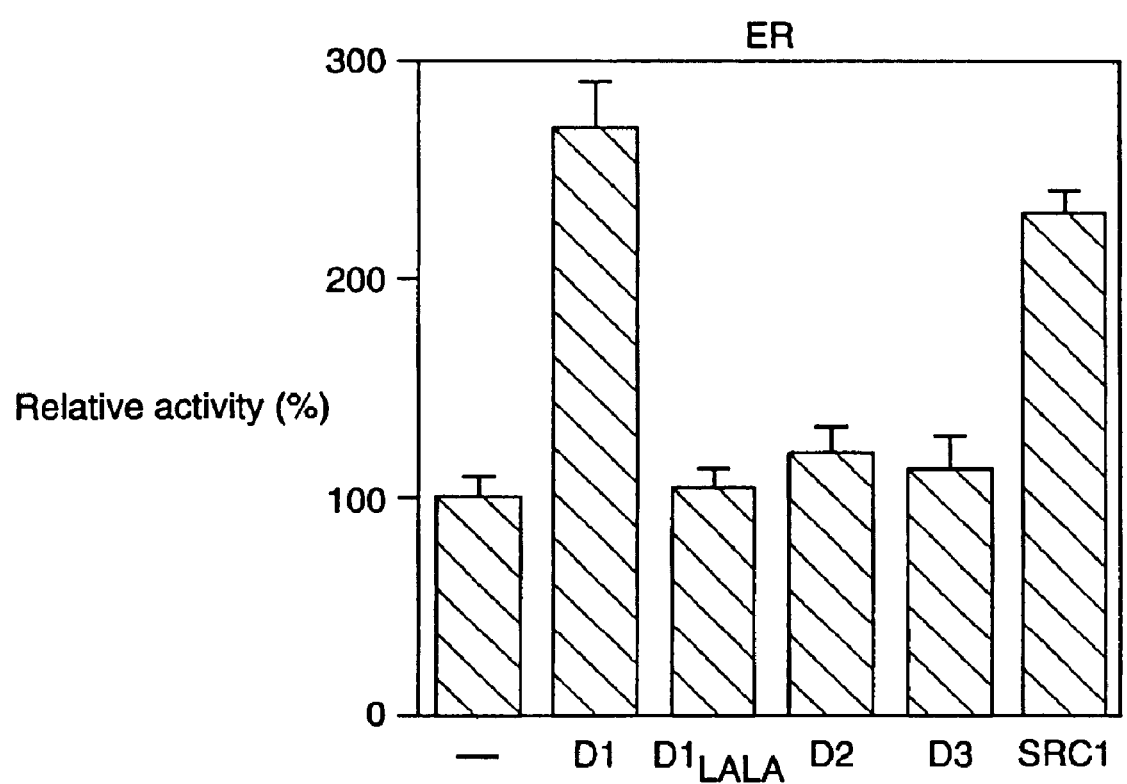

COS: ER 1-535

COS: ER L543/544A

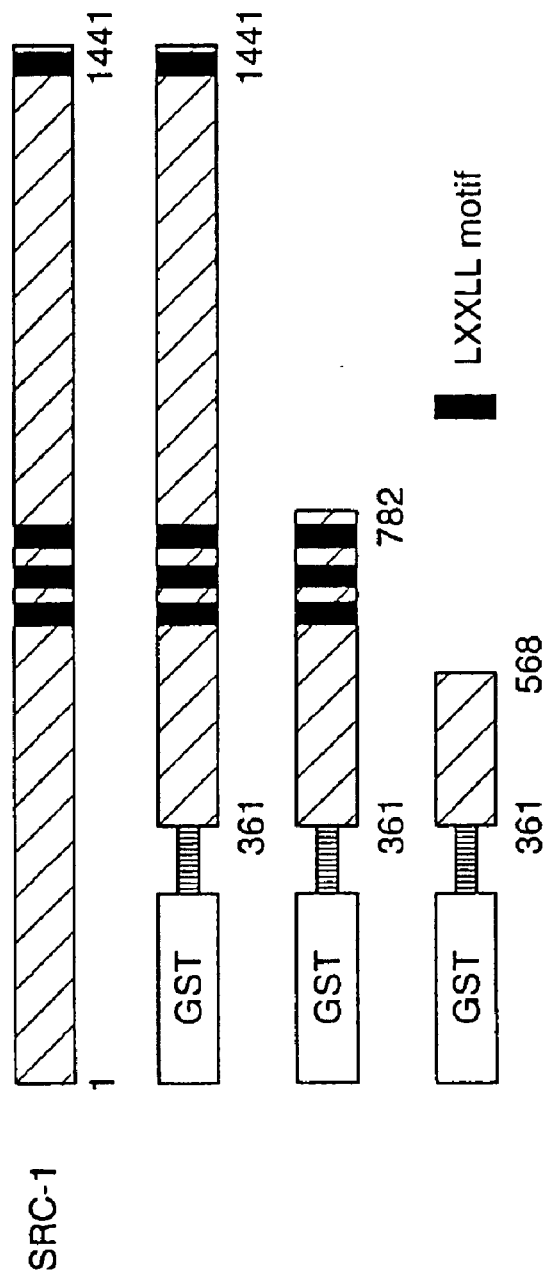

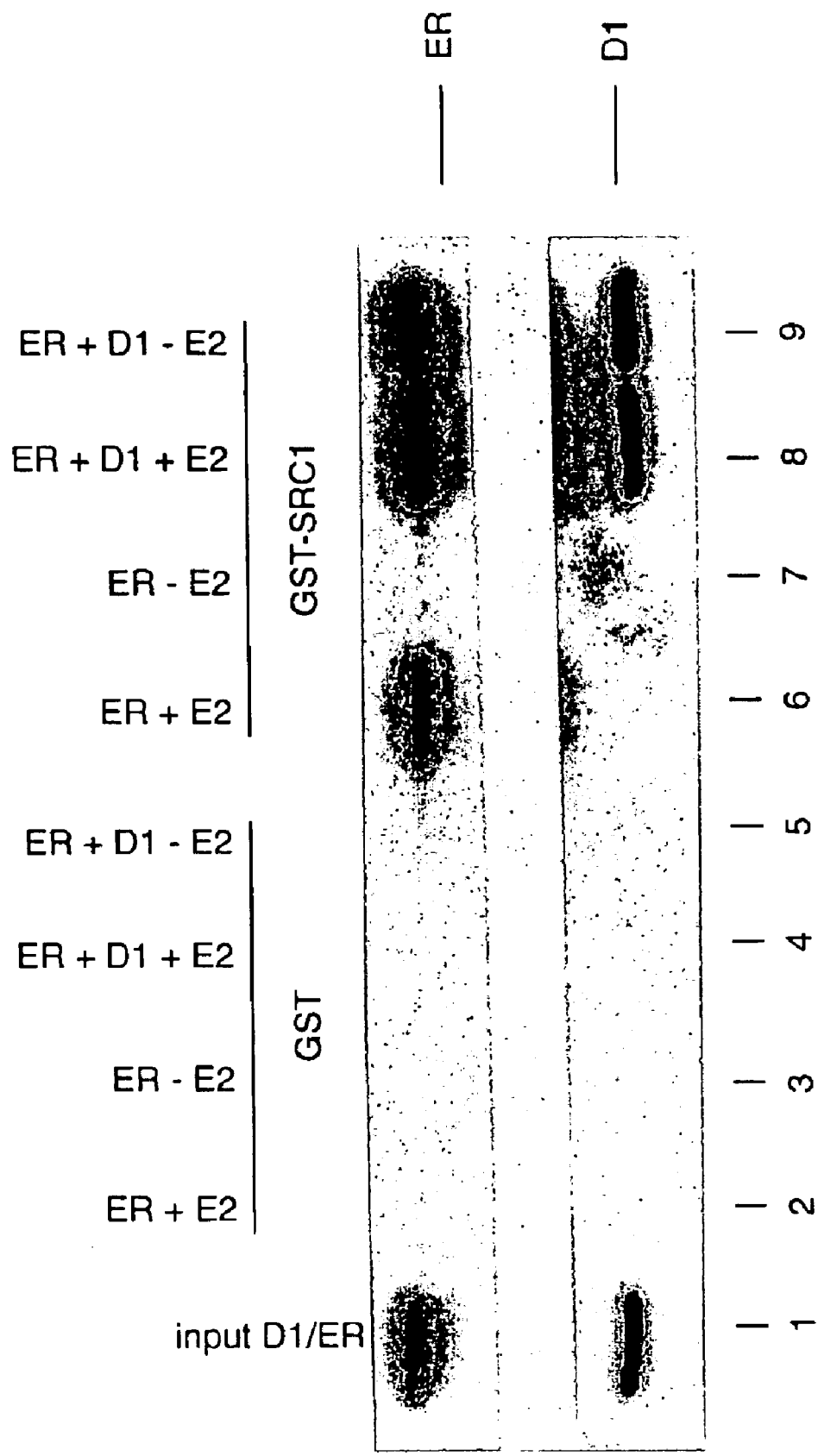

FIG. 7
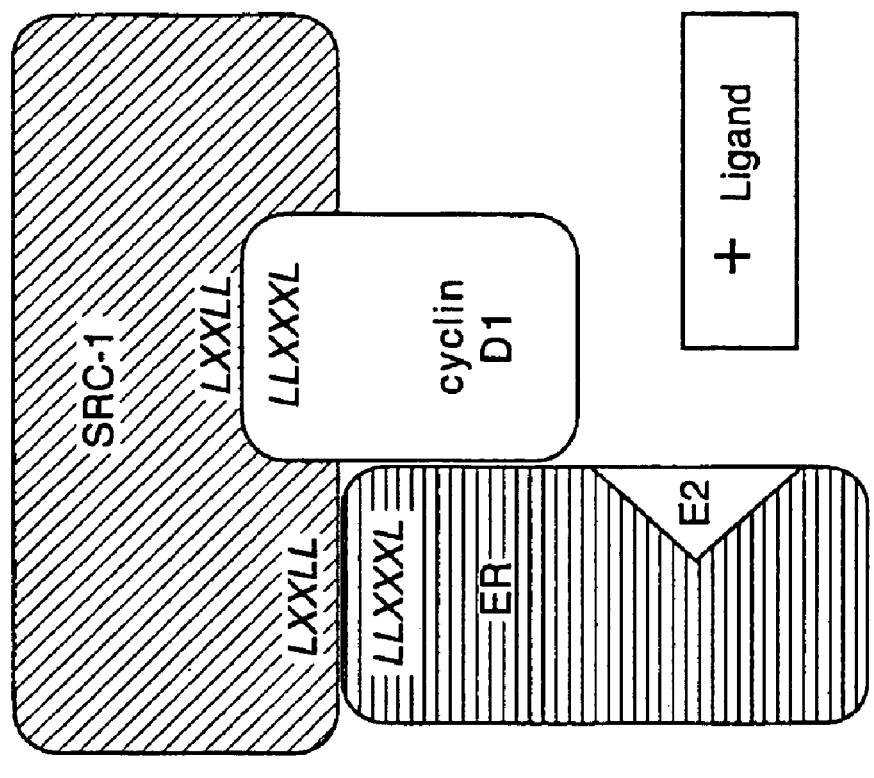
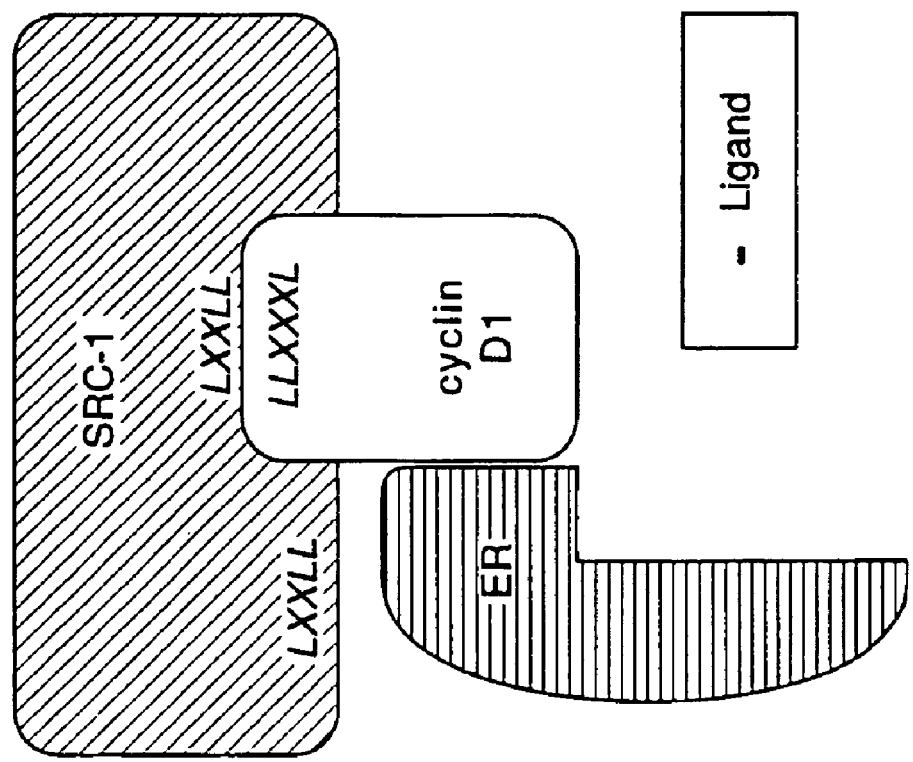

SEQUENCE LISTING

```
<160> NUMBER OF SEQ ID NOS: 27

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence:Peptide
      containing an LXXLL motif found in steroid
      receptor coactivators

<400> SEQUENCE: 1

Ala Ala Ser Lys His Lys Gln Leu Ser Glu Leu Leu Arg Ser Gly
  1               5                  10                  15

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence:Peptide
      containing an LXXLL motif found in steroid
      receptor coactivators

<400> SEQUENCE: 2

Ser His Lys Leu Val Gln Leu Leu Thr Thr Thr Ala Glu Gln
  1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:Peptide
      containing an LXXLL motif found in steroid
      receptor coactivators

<400> SEQUENCE: 3

Glu Arg His Lys Ile Leu His Arg Leu Leu Gln Glu Gly Ser
  1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence:Peptide
      containing an LXXLL motif found in steroid
      receptor coactivators

<400> SEQUENCE: 4

Lys Asp His Gln Leu Leu Arg Tyr Leu Leu Asp Lys Asp Glu
  1               5                  10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence:Peptide
      containing an LXXLL motif found in steroid
      receptor coactivators
```

```
<400> SEQUENCE: 5

Pro Gln Ala Gln Gln Lys Ser Leu Gln Gln Leu Leu Thr
 1               5                  10

<210> SEQ ID NO 6
<211> LENGTH: 5
<212> TYPE: PRT
<213> ORGANISM: Artificial Sequence
<220> FEATURE:
<221> NAME/KEY: DOMAIN
<222> LOCATION: (2)..(3)
<223> OTHER INFORMATION: LXXLL is a motif found in steroid receptor
      coactivators that is involved in nuclear receptor
      interaction, where X at positions 2 and 3 can be
      any amino acid
<223> OTHER INFORMATION: Description of Artificial Sequence:Motif found
      in steroid receptor activators

<400> SEQUENCE: 6

Leu Xaa Xaa Leu Leu
 1               5

<210> SEQ ID NO 7
<211> LENGTH: 6
<212> TYPE: PRT
<213> ORGANISM: Artificial Sequence
<220> FEATURE:
<221> NAME/KEY: DOMAIN
<222> LOCATION: (2)..(4)
<223> OTHER INFORMATION: LXXXLL is a motif found in cyclin D1 that
      interacts with steroid receptor coactivators,
      where X at positions 2 to 4 can be any amino acid
<223> OTHER INFORMATION: Description of Artificial Sequence:Motif in
      cyclin D1

<400> SEQUENCE: 7

Leu Xaa Xaa Xaa Leu Leu
 1               5

<210> SEQ ID NO 8
<211> LENGTH: 6
<212> TYPE: PRT
<213> ORGANISM: Homo sapiens
<220> FEATURE:
<221> NAME/KEY: DOMAIN
<222> LOCATION: (1)..(6)
<223> OTHER INFORMATION: Human cyclin D1 LLXXXL motif

<400> SEQUENCE: 8

Leu Leu Glu Ser Ser Leu
 1               5

<210> SEQ ID NO 9
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: Peptide based on LXXLL motif found in steroid
      receptor coactivators, X at positions 1-8, 10, 11, 14-21 can be any
      amino acid

<400> SEQUENCE: 9

Xaa Xaa Xaa Xaa Xaa Xaa Xaa Xaa Leu Xaa Xaa Leu Leu Xaa Xaa Xaa
 1               5                  10                  15

Xaa Xaa Xaa Xaa Xaa
            20
```

```
<210> SEQ ID NO 10
<211> LENGTH: 16
<212> TYPE: PRT
<213> ORGANISM: Drosophila melanogaster
<220> FEATURE:
<221> NAME/KEY: PEPTIDE
<222> LOCATION: (1)..(16)
<223> OTHER INFORMATION: Translocation peptide derived from antennapedia
      homeodomain protein

<400> SEQUENCE: 10

Arg Gln Ile Lys Ile Trp Phe Gln Asn Arg Arg Met Lys Trp Lys Lys
 1               5                  10                  15

<210> SEQ ID NO 11
<211> LENGTH: 9
<212> TYPE: PRT
<213> ORGANISM: Homo sapiens

<400> SEQUENCE: 11

Glu Ala Leu Leu Glu Ser Ser Leu Arg
 1               5

<210> SEQ ID NO 12
<211> LENGTH: 9
<212> TYPE: PRT
<213> ORGANISM: Homo sapiens

<400> SEQUENCE: 12

Tyr Asp Leu Leu Leu Glu Met Leu Asp
 1               5

<210> SEQ ID NO 13
<211> LENGTH: 9
<212> TYPE: PRT
<213> ORGANISM: Homo sapiens

<400> SEQUENCE: 13

Glu Ala Val Leu Leu Asn Ser Leu Gln
 1               5

<210> SEQ ID NO 14
<211> LENGTH: 9
<212> TYPE: PRT
<213> ORGANISM: Homo sapiens

<400> SEQUENCE: 14

Glu Ala Ala Leu Arg Glu Ser Leu Arg
 1               5

<210> SEQ ID NO 15
<211> LENGTH: 14
<212> TYPE: PRT
<213> ORGANISM: Homo sapiens

<400> SEQUENCE: 15

Ser His Lys Leu Val Gln Leu Leu Thr Thr Thr Ala Glu Gln
 1               5                  10

<210> SEQ ID NO 16
<211> LENGTH: 14
<212> TYPE: PRT
<213> ORGANISM: Homo sapiens

<400> SEQUENCE: 16
```

-continued

Glu Arg His Lys Ile Leu His Arg Leu Leu Gln Glu Gly Ser
 1               5                   10

<210> SEQ ID NO 17
<211> LENGTH: 14
<212> TYPE: PRT
<213> ORGANISM: Homo sapiens

<400> SEQUENCE: 17

Lys Asp His Gln Leu Leu Arg Tyr Leu Leu Asp Lys Asp Glu
 1               5                   10

<210> SEQ ID NO 18
<211> LENGTH: 13
<212> TYPE: PRT
<213> ORGANISM: Homo sapiens

<400> SEQUENCE: 18

Pro Gln Ala Gln Gln Lys Ser Leu Gln Gln Leu Leu Thr
 1               5                   10

<210> SEQ ID NO 19
<211> LENGTH: 13
<212> TYPE: PRT
<213> ORGANISM: Homo sapiens

<400> SEQUENCE: 19

Pro Gln Ala Gln Gln Lys Ser Leu Gln Gln Ala Ala Thr
 1               5                   10

<210> SEQ ID NO 20
<211> LENGTH: 6
<212> TYPE: PRT
<213> ORGANISM: Artificial Sequence
<220> FEATURE:
<221> NAME/KEY: DOMAIN
<222> LOCATION: (3)..(5)
<223> OTHER INFORMATION: Leucine-rich coactivator binding site where Xaa
      at positions 3-5 can be any amino acid
<223> OTHER INFORMATION: Description of Artificial Sequence:Motif of
      leucine-rich coactivator binding site

<400> SEQUENCE: 20

Leu Leu Xaa Xaa Xaa Leu
 1               5

<210> SEQ ID NO 21
<211> LENGTH: 6
<212> TYPE: PRT
<213> ORGANISM: Homo sapiens
<220> FEATURE:
<221> NAME/KEY: DOMAIN
<222> LOCATION: (3)..(5)
<223> OTHER INFORMATION: Leucine-rich coactivator site in an estrogen
      receptor, where X at positions 3-5 can be any
      amino acid

<400> SEQUENCE: 21

Ala Ala Xaa Xaa Xaa Leu
 1               5

<210> SEQ ID NO 22
<211> LENGTH: 5
<212> TYPE: PRT
<213> ORGANISM: Artificial Sequence
<220> FEATURE:
<221> NAME/KEY: PEPTIDE
<222> LOCATION: (2)..(3)

```
<223> OTHER INFORMATION: Mutant peptide of LXXLL steroid receptor
      coactivator motif, where X at positions 2 and 3
      can be any amino acid
<223> OTHER INFORMATION: Description of Artificial Sequence:Motif of
      steroid receptor coactivator

<400> SEQUENCE: 22

Leu Xaa Xaa Ala Ala
 1               5

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:Peptide
      containing a LXXAA variant of the LXXLL motif
      found in steroid receptor coactivators.

<400> SEQUENCE: 23

Ala Ala Ser Lys His Lys Gln Leu Ser Glu Ala Ala Arg Ser Gly
 1               5                  10                  15

<210> SEQ ID NO 24
<211> LENGTH: 9
<212> TYPE: PRT
<213> ORGANISM: Artificial Sequence
<220> FEATURE:
<223> OTHER INFORMATION: Leucine Rich Motif of Cyclin D1 mutant

<400> SEQUENCE: 24

Glu Ala Leu Leu Glu Ser Ser Leu Arg
 1               5

<210> SEQ ID NO 25
<211> LENGTH: 9
<212> TYPE: PRT
<213> ORGANISM: Artificial Sequence
<220> FEATURE:
<223> OTHER INFORMATION: Leucine Rich Motif of Estrogen receptor mutant

<400> SEQUENCE: 25

Tyr Asp Leu Leu Leu Glu Met Leu Asp
 1               5

<210> SEQ ID NO 26
<211> LENGTH: 9
<212> TYPE: PRT
<213> ORGANISM: Artificial Sequence
<220> FEATURE:
<223> OTHER INFORMATION: Leucine Rich Motif of Cyclin D2 mutant

<400> SEQUENCE: 26

Glu Ala Val Leu Leu Asn Ser Leu Gln
 1               5

<210> SEQ ID NO 27
<211> LENGTH: 9
<212> TYPE: PRT
<213> ORGANISM: Artificial Sequence
<220> FEATURE:
<223> OTHER INFORMATION: Leucine Rich Motif of Cyclin D3 mutant

<400> SEQUENCE: 27

Glu Ala Ala Leu Arg Glu Ser Leu Arg
 1               5
```

INTERACTION BETWEEN CYCLIN D1 AND STEROID RECEPTOR CO-ACTIVATORS AND USES THEREOF IN ASSAYS

This is a continuation of U.S. patent application Ser. No. 09/302,305, filed on Apr. 30, 1999 now U.S. Pat. No. 6,350,572, is a continuation of PCT Application No. PCT/GB99/00440, filed 12 Feb. 1999; which in turn claims priority from Great Britain Patent Application No. GB 9803035.6, filed 12 Feb. 1998, and Great Britain Patent Application No. GB 9818243.9, filed 20 Aug. 1998.

The present invention relates to methods for preventing the growth of tumours, and for assays for compounds useful in the prevention of tumours.

BACKGROUND TO THE INVENTION

The cyclins are a class of polypeptides which are involved in the control of the cell cycle. Three closely related human D-type cyclins have been identified, all of which interact with and activate cyclin dependent kinases (CDK) 4 and 6, although they have specialized function in distinct cell types. The cyclin D1 gene has been found to be overexpressed and/or deregulated by clonal chromosome rearrangements or by amplification in B cell lymphoma, in parathyroid adenoma, and in breast and squamous cell cancer. It has also recently been shown that cyclin D1 deficient mice have a defect in estrogen-mediated proliferation of breast epithelium during pregnancy (Sicinski et al, 1995, Cell 82; 621–630; Fantl et al, 1995, Genes & Development 9; 2364–2372).

Cyclin D1 is induced in response to mitogenic stimulation of quiescent cells and acts as an activator of CDK4 and CDK6. These cyclin D1/CDK complexes are key regulators of progression through the GI phase of the cell cycle and are involved in functional inactivation of the retinoblastoma family proteins (reviewed in (Beijersbergen and Bernards, 1996)). Cyclin D1 is amplified or over-expressed in a number of human malignancies, the most prominent being breast cancer, in which up to 50% of all cases have elevated levels of cyclin D1 (Buckley et al., 1993; Schuuring et al., 1992; van Diest et al., 1997). The relevance of cyclin D1 over-expression is underscored by the finding that tissue-specific transgenic expression of cyclin D1 in mice results in mammary hyperplasia and adenocarcinoma (Wang et al., 1994). Furthermore, cyclin D1 knockout mice show a marked defect in breast epithelium development during pregnancy and cyclin D1 reduces mitogen requirement of breast cancer cell lines (Fantl et al., 1995; Musgrove et al., 1994; Sicinski et al., 1995; Zwijsen et al., 1996). Cyclin D1 is over-expressed preferentially in ER-positive breast cancers, suggesting that cyclin D1 derives (part of) its oncogenic activity in breast cancer by acting on ER (Gillett et al., 1996; van Diest et al., 1997). We and others have recently made a connection between ER and cyclin D1 by showing that cyclin D1 can interact directly with the ligand binding domain of ER and can stimulate ER transactivation in a ligand-independent and CDK-independent fashion (Neuman et al., 1997; Zwijsen et al., 1997).

WO97/40378 also discloses that cyclin D1 interacts with the estrogen receptor (ER). Transcription is increased by formation of cyclin D1-ER complex which binds to the estrogen response element (ERE) found upstream of estrogen responsive genes. This finding provides a target for the control of cell proliferation, particularly in those cells which grow in response to stimulation by estrogen, e.g. breast tumour cells.

Several lines of evidence suggest that efficient transactivation requires additional positively acting factors termed coactivators (Pugh and Tjian, 1990). Several candidate steroid receptor coactivators (SRCs) have been identified. The first coactivator identified based on its ability to interact with the progesterone receptor was SRC-1 (Onate et al., 1995; Yao et al., 1996). This protein is the founding member of a family of related SRCs that include TIF-2/GRIP-1 (Hong et al., 1997; Voegel et al., 1996) and AIB-1/ACTR/RAC-3/p/CIP (Anzick et al., 1997; Chen et al., 1997; Li et al., 1997; Torchia et al., 1997). Several functional domains are highly conserved in all members of this family. For instance, the N-terminal regions contain basic helix-loop-helix (bHLH) and per-ARNT-Sim (PAS) domains. Both motifs are thought to be involved in protein-protein interactions and DNA-protein interactions (Yao et al., 1996). Interestingly, the bHLH-PAS domain is dispensable for SRC-1 activity, including receptor interaction and receptor activation (Onate et al., 1995; Yao et al., 1996). In addition, all SRCs contain multiple LXXLL (SEQ ID NO:6)motifs (L is leucine; X is any amino acid) in the central region of the protein. These motifs were recently shown to be involved in nuclear receptor interaction (Heery et al., 1997; Le Douarin et al., 1996; Torchia et al., 1997). Besides ER, SRC-1 also interacts with another coactivator of steroid receptors, CDP/p300, and both types of coactivators act synergistically to enhance ER transactivation (Chakravarti et al., 1996; Chen et al., 1997; Hanstein et al., 1996; Kamei et al., 1996; Smith et al., 1996; Yao et al., 1996). Both coactivators of the SRC-1 family and the p300/CBP family have intrinsic histone acetyl transferase (HAT) activity which is widely believed to be involved in chromatin remodeling during transcriptional activation (Jenster et al., 1997; Ogryzko et al., 1996; Spencer et al., 1997).

DISCLOSURE OF THE INVENTION

We have continued to investigate the mechanism of ER activation by cyclin D1 and found that surprisingly, there is also a direct interaction between SRC-1 and cyclin D1. This interaction appears to be mediated primarily through the LXXLL motifs of SRC-1. We have also found evidence that other SRCs, particlarly AIB-1.and TIF-2 (which also have LXXLL motifs) bind to cyclin D1 in a similar manner. The direct interaction of cyclin D1 with SRCs enhances ER mediated transcription. The interaction provides a novel target for the development of assays for substances which modulate the cell cycle, particularly in cells which grow in response to stimulation by estrogen, e.g. breast tumour cells.

Thus the present invention is useful for assaying for potential modulators of the growth of estrogen responsive tumour cells, particularly those in which cyclin D1 is found at elevated levels. Elevated levels of cyclin D1 may occur for a variety of reasons, e.g. over-expression of a single cyclin D1 gene or by gene amplification.

Thus in a first aspect the present invention provides an assay for a modulator of estrogen responsive tumour cells which comprises:

a) bringing into contact a cyclin D1, an SRC and a putative modulator compound under conditions where the cyclin D1 and the SRC, in the absence of modulator, are capable of forming a complex; and b) measuring the degree of inhibition of complex formation caused by said modulator compound.

The present invention further provides an assay for a modulator of estrogen responsive tumour cells which comprises:

a) bringing into contact a cyclin D1, an SRC, an estrogen receptor and a putative modulator compound under conditions where the cyclin, the SRC and the estrogen receptor, in the absence of modulator, are capable of forming a complex which is capable of binding to an estrogen response element;
b) providing an estrogen response element to which the complex is capable of binding and transcriptionally activating; and
c) measuring the degree of inhibition of binding or transcriptional activation caused by said modulator compound.

In a further aspect, the invention provides compounds obtainable by such an assay, for example peptide compounds based on the portions of cyclin D1, an SRC, or the estrogen receptor which interact with each other.

The assay of the invention is optionally performed in the presence of an estrogen which is capable of binding to the estrogen receptor.

DETAILED DESCRIPTION OF THE INVENTION

Cyclin D1

The cyclin D1 may be any suitable mammalian cyclin D1, particularly human cyclin D1. Human D1 cyclin has been cloned and sources of the gene can be readily identified by those of skill in the art. See for example, Xiong et al, 1991, Cell 65; 691–699 and Xiong et al, 1992, Genomics 13; 575–84. Murine D1 cyclin has also been cloned. Other mammalian cyclins can be obtained using routine cloning methods analogous to those described in the aforementioned references.

Although wild-type cyclin D1 is preferred mutants and variants of D1 which still retain the ability to interact directly with the estrogen receptor may also be used. Examples of cyclin D1 mutants are well known in the art and two particular mutants are illustrated in WO97/40378. A particularly preferred mutant is a mutant which carries a mutation in the cyclin box, such as the cyclin D1-KE mutant. This mutation renders the D1 unable to bind CDKs.

Mutants and other variants will generally be based on wild-type mammalian cyclin D1s and have a degree of amino acid identity which is desirably at least 70%, preferably at least 80%, 90%, 95% or even 98% homologous to a wild type mammalian cyclin.

It is not necessary to use the entire cyclin D1 proteins (including their mutants and other variants) for assays of the invention. Fragments of the cyclin may be used provided such fragments retain the ability to interact with the target domain of the SRC and desirably also the estrogen receptor responsible for the cyclin interaction. Fragments of cyclin D1 may be generated in any suitable way known to those of skill in the art. Suitable ways include, but are not limited to, recombinant expression of a fragment of the DNA encoding the cyclin. Such fragments may be generated by taking DNA encoding the cyclin, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments of the cyclin (up to about 20 or 30 amino acids) may also be generated using peptide synthesis methods which are well known in the art. Generally fragments will be at least 40, preferably at least 50, 60, 70, 80 or 100 amino acids in size.

Particularly preferred fragments include those which are based upon the C-terminal region of cyclin D1, said region including the C-terminal motif LLXXXL (SEQ ID NO.7), which in human cyclin D1 is represented by the sequence LLESSL (SEQ ID NO:8) at residues 254–259. These fragments will be able to interact with the SRC and desirably also the ER. Desirably the fragments comprise the C-terminal region of cyclin D1.

The ability of suitable fragments to bind to the SRC (or fragment thereof) may be tested using routine procedures such as those described in the accompanying examples relating to intact cyclin D1. Reference herein to cyclin D1 includes the above mentioned mutants and fragments which are functionally able to bind the SRC unless the context is explicitly to the contrary.

SRC Protein

The SRC protein may be any human or other mammalian protein, or fragment thereof which has the ability to bind to a steroid receptor and cyclin D1, and enhance the receptor's transcriptional activity. A number of SRC proteins have been cloned. These include SRC-1, the sequence of which is shown in Onate et al, *ibid*, 1995; TIF-2, the sequence of which is shown in Voegel et al, *ibid*, 1996, and AIB-1 (also called ACTR), the sequence of which is shown in Chen et al, *ibid*, 1997. These are all human SRC proteins. The sequence of the murine homologue of TIF-2 is disclosed in Hong et al, *ibid*, 1997 (where it is called GRIP-1), and the sequence of the murine homologue of AIB-1 is disclosed in Torchia et al, *ibid*, 1997 (where it is called P/CIP).

There are a number of common structural features found in the SRC proteins identified to date. These include an N-terminal region of about 300 amino acids comprising the bHLH and PAS regions mentioned above. A comparision of these domains is shown in Chen et al, *ibid*. The AIB-1 bHLH/PAS domain shares about 65% homology (identity) with the corresponding TIF-2 domain and about 58% homology (identity) with the corresponding SRC-1 domain.

The central portion of the proteins (from about amino acids 570 to 780 of SRC-1) comprises a receptor interaction domain (RID) which also appears to be primarily responsible for the physical interaction with cyclin D1. The AIB-1 RID has 42% and 27% amino acid identity with the TIF-2 and SRC-1 RIDs respectively.: The RIDs comprise three motifs which share the common primary sequece LXXLL (SEQ ID NO:6).

The SRCs also have, C-terminal to the central portion, a histone acetyl transferase domain.

Thus an SRC protein in its broadest sense is one which has, in N- to C-terminal order, a bHLH/PAS domain of about 300 amino acids with at least 50% homology to the corresponding domain of SRC-1, AIB-1 or TIF-2; a centrally located RID of about 210 amino acids with one or more, such as three, LXXLL (SEQ ID NO:6) motifs; and a domain which has HAT activity.

Variants of the above SRCs may be used, such as synthetic variants which have at least 50% amino acid identity to a naturally occurring SRC (particularly a human SRC), preferably at least 60%, 70%, 80%, 90%, 95% or 98% identity. The assay preferably uses the same mammalian source SRC as the cyclin D1. A preferred subset of variants are those which retain one or more of the motifs LXXLL (SEQ ID NO:6) of the central portion, and preferably retains three as found in the SRCs mentioned above. The variants may also be manipulated to provide more than three, for example, four, five or six, LXXLL (SEQ ID NO:6) motifs. These additional motifs will preferably be within the RID domain, but may also be introduced in other portions of an SRC protein. The motifs may be introduced by insertion of additional amino acids of by substitution of amino acids within the SRC.

Fragments of the SRC protein and its variants may be used, provided that said fragments retain the ability to interact with a wild-type cyclin D1, preferably wild-type human cyclin D1. Such fragments are desirably at least 50, preferably at least 75, 100, 200, 250 or 400 amino acids in size. Desirably such fragments include one or more of the (such as all three of the centrally located) LXXLL (SEQ ID NO:6) motifs.

Estrocren Receptor

The estrogen receptor used in the assay may be obtained from the same mammalian source as the cyclin D1. The human estrogen receptor is preferred. This is a 66 kd protein which functions as hormone-activated transcription factor, the sequence of which is published in the art and is generally available. Receptor activation is thought to be a consequence of ligand-induced conformational changes in the structure of the receptor. The complex of estrogen with its receptor binds to specific DNA sequences including, with high affinity, to a well-defined 13-bp palindromic sequence—the estrogen response element (ERE). The ERE is usually located upstream of an estrogen-responsive gene. Estrogen responsive genes include progesterone receptor and PS-2. Transcriptional activation of these genes is involved in estrogenresponsive tumour growth.

There is also a second estrogen receptor, ER beta. This is disclosed in Kuiper et al, 1996. The ERβ may also be used, and is included herein when reference is made to the ER.

Fragments and variants of the estrogen receptor which retain the ability to interact with the cyclin D1 may also be used, and such fragments and mutants may be obtained by methods analogous to those described above in relation to cyclin fragments.

Variants of ER include a number of variants which have been found to be associated with breast cancer. Some of these are associated with breast cancers which are resistant to anti-estrogen therapies, particularly tamoxifen therapies. Variants are disclosed in, for example, McGuire et al, 1991; Fuqua et al, 1993; and Miksicek et al, 1995.

Mutants and other variants of ER will generally be based on wild-type mammalian ERs and have a degree of amino acid identity which is desirably at least 70%, preferably at least 80%, 90%, 95% or even 98% homologous to a wild type mammalian ER.

Particluarly preferred fragments (including fragments of the above-described variants) include those which retain the E/F regions comprising amino acids 292–595 or a portion thereof such as 340–595 of the ER. Smaller fragments may also be used, e.g. those starting at around 292, 300, 340, 360 or 380 and ending at the C-terminus (595) or a truncation thereof, e.g. 590, 580, 550 or 500. Suitable fragments may be determined by routine experimentation. Reference herein to the estrogen receptor includes fragments and mutants which retain the ability to interact with cyclin D1 unless the context is explicitly to the contrary. In this context, "interact" includes binding to ER, the minimum requirement for an in vitro assay. For in vitro or in vivo assays which rely on the D1-SRC-ER complex binding to an ERE and activating transcription, the necessary interaction must provide this.

In an alternative format the ER may be added in the form of two partial proteins, for example expressed from two partial ER expression vectors. The first protein encodes the N-terminal region of ER (containing AF-1 and the DNA binding region), the second the C-terminal part (containing AF-2 and the hormone binding region). The hormone binding region is optionally linked to an activator protein such as the GAL4 activation domain or the VP16 activation domain. As illustrated in the accompanying examples, ERE-dependent transcription is stimulated by both cyclin D1 and an SRC protein, and the presence of both components synergistically enhances the activation. Thus putative modulators may be used and the decrease in the synergistic enhancement of activation may be observed in assays of the present invention.

Estrogens

Although we previously have found that the estrogen receptor is activated by cyclin D1 alone to provide ERE-responsive gene transcription we have found that transcription is enhanced synergistically in the presence of an estrogen. It is thus a preferred aspect of the assay that estrogen is also brought into contact with the cyclin D1, SRC, estrogen receptor and putative inhibitor compound when a transcriptional acitivation assay of the invention is performed. The estrogen may be any natural or synthetic estrogen capable of binding to and activating the estrogen receptor. Examples of estrogens include 17β-estradiol.

Assay Formats

One assay format which is widely used in the art to study the a interaction of two proteins is a two-hybrid assay. This assay may be adapted for use in the present invention. A two-hybrid assay comprises the expression in a host cell of the the two proteins, one being a fusion protein comprising a DNA binding domain (DBD), such as the yeast GAL4 binding domain, and the other being a fusion protein comprising an activation domain, such as that from GAL4 or VP16. In such a case the host cell (which again may be bacterial, yeast, insect or mammalian, particularly yeast or mammalian) will carry a reporter gene construct with a promoter comprising a DNA binding elements compatible with the DBD. The reporter gene may be a reporter gene such as chloramphenical acetyl transferase, luciferase, green fluorescent protein (GFP) and β-galactosidase, with luciferase being particularly preferred.

Two-hybrid assays may be in accordance with those disclosed by Fields and Song, 1989, Nature 340; 245–246. In such an assay the DNA binding domain (DBD) and the transcriptional activation domain (TAD) of the yeast GAL4 transcription factor are fused to the first and second molecules respectively whose interaction is to be investigated. A functional GAL4 transcription factor is restored only when two molecules of interest interact. Thus, interaction of the molecules may be measured by the use of a reporter gene operably linked to a GAL4 DNA binding site which is capable of activating transcription of said reporter gene.

Thus two hybrid assays may be performed in the presence of a potential modulator compound and the effect of the modulator will be reflected in the change in transcription level of the reporter gene construct compared to the transcription level in the absence of a modulator.

Host cells in which the two-hybrid assay may be conducted include mammalian, insect and yeast cells, with yeast cells (such as S. cerivissiae and S. pombe) being particularly preferred.

In the case of the present invention, a two-hybrid assay will be conducted by fusing the cyclin D1 protein being used to a DNA-binding domain and the SRC protein to the activation domain.

Another assay format measures directly, in vivo or in vitro the interaction between cyclin D1 and the SRC by labelling one of these proteins with a detectable label and bringing it into contact with the other protein which has been optionally immobilised on a solid support, either prior to or after proteins have been brought into contact with each other. Suitable detectable labels include $^{35}$S-methionine which may be incorporated into recombinantly produced proteins, and tags such as an HA tag, GST or histidine. The recombinantly produced protein may also be expressed as a fusion protein containing an epitope which can be labelled with an antibody. Alternatively, an antibody against the cyclin and/or SRC can be obtained using conventional methodology.

The protein which is optionally immobilized on a solid support may be immobilized using an antibody against that protein bound to a solid support or via other technologies which are known per se. In the Examples which follow a preferred in vitro interaction is illustrated which utilises a fusion protein of SRC-1 fused to glutathione-S-transferase (GST). This may be immobilized on glutathione agarose beads. In an in vitro assay format of the type described above the putative inhibitor compound can be assayed by determining its ability to diminish the amount of labelled cyclin D1 which binds to the immobilized GST-SRC-1. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present, in, for example, a suitable scintillation counter.

Another assay format is dissociation enhanced lanthanide fluorescent immunoassay (DELFIA) (Ogata et al, 1992). This is a solid phase based system for measuring the interaction of two macromolecules. Typically one molecule (either SRC1 or cyclin D1) is immobilised to the surface of a multi well plate and the other molecule is added in solution to this. Detection of the bound partner is achieved by using a label consisting of a chelate of a rare earth metal. This label can be directly attached to the interacting molecule or may be introduced to the complex via an antibody to the molecule or to the molecules epitope tag. Alternatively, the molecule may be attached to biotin and a streptavidin-rare earth chelate used as the label. The rare earth used in the label may be europium, samarium, terbium or dysprosium. After washing to remove unbound label, a detergent containing low pH buffer is added to dissociate the rare earth metal from the chelate. The highly fluorescent metal ions are then quantitated by time resolved fluorimetry. A number of labelled reagents are commercially available for this technique, including streptavidin, antibodies against glutathione-S-transferase and against hexahistidine.

In an alternative mode, the one of the cyclin D1 and the SRC may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when the cyclin D1 and an SRC interact. The presence of a candidate modulator compound which modulates the interaction will increase or decrease the amount of unaltered fluorescence signal of the donor.

FRET is a technique known per se in the art and thus the precise donor and acceptor molecules and the means by which they are linked to the cyclin D1 and an SRC may be accomplished by reference to the literature.

Suitable fluorescent donor moieties are those capable of transferring fluorogenic energy to another fluorogenicmolecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivatives, aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label the cyclin D1 and ER. For attachment of carbocyanine, see for example Guo et al, J. Biol. Chem., 270; 27562–8, 1995.

The assays described above may also utilise the requirement of SRC and ER for an estrogen if binding of ER to the estrogen response element (ERE) is to occur. We have found that the binding of ER to the ERE is independent of estrogen when either cyclin D1 is present, or both cyclin D1 and an SRC are present. The binding of ER to the ERE provides the basis for a binding assay. For example, a detectably labelled ERE may be brought into contact with ER, cyclin D1 and an SRC under conditions where, in the absence of an inhibitor, a complex of the three components is detectable on the ERE. The ERE is preferably labelled with a label which allows physical recovery of the ERE, for example with a paramagnetic bead or a protein which may be reversibly or irreversibly attached to a solid support such as a chromatography column.

Once the ERE is recovered, the proteins still associated with it may be recovered and the presence or absence of specific components of the complex determined. Protein components may conveniently be examined by Western blotting. Alternatively, immunological means may be used. In another alternative, the different protein components may be labelled with different fluorogenic or radioactive label, which may be detected with little or no separation of the recovered ERE-protein complex.

Such assays may be used to determine whether, in the presence of a putative modulator compound, the SRC remains bound to cyclin D1 in the ternary complex.

The assay of the invention may also take the form of an in vivo assay based on the ability of the complex of the ER, cyclin D1 and the SRC to activate estrogen responsive transcription. The term "in vivo" includes cell lines and the like, and excludes whole humans. The in vivo assay may be performed in an estrogen responsive cell line which expresses the estrogen receptor or in ER-negative cell lines in which the ER is expressed from a vector introduced into the cell. The cell line may be in tissue culture or may be a cell line xenograft in a non-human animal subject.

Where a cell line expressing the estrogen receptor is used a reporter gene construct comprising an ERE operably linked to a reporter gene may be introduced into the cell together with vector(s) for the expression of a cyclin D1 and an SRC. These proteins may be expressed from a single vector or from two separate vectors. The vector(s) may utilize any suitable promoter, such as described herein. Two or more EREs (for example 3, 4 or 5) may be present in the receptor construct and this may enhance sensitivity of the assay. The reporter gene may be any suitable reporter gene used in the art. Such reporter genes includes chloramphenicol acetyl transferase (CAT), β-galactosidase, luciferase or GFP. The cyclin D1 expression vector will comprise DNA encoding cyclin operably linked to a promoter capable of expressing the gene in the host cell. Suitable promoters include viral promoters such as a CMV or SV40 promoter.

The cell lines used in assays of the invention may be used to achieve transient expression of the cyclin although in a further aspect of the invention cells which are stably transfected with constructs which express a D1 and SRC and, where required, the ER may also be generated. Means to generated stably transformed cell lines are well known in the art and such means may be used here.

Suitable cell lines include breast cancer cell lines which are widely available in the art. The Examples which follow utilise the T47D breast cancer cell line although other suitable Examples include MCF-7 and MDA. Such assays may also be performed in cell free systems such as a reticulocyte cell free system.

Where the cell line does not express ER, a construct capable of expressing this protein may also be introduced into the cell operably linked to a suitable promoter.

The precise format of the assays of the invention may be varied by those of skill in the art using routine skill and knowledge. In the in vitro assays of the invention, the amount of cyclin D1, SRC and, where required, estrogen receptor may be varied depending upon the scale of the assay. In general, the person of skill in the art will select relatively equimolar amounts of the two components, say from 1:10 to 100:1, preferably from 1:1 to 10:1, molar ratio of cyclin D1 to SRC. However there may be particular assay formats which can be practiced outside this range.

In the in vivo assays of the invention, it will be desirable to achieve sufficient expression of cyclin D1 to recruit sufficient SRC to a complex with ER that the effect of a putative modulator compound may be measured. Where the cell does not express ER, sufficient expression of this will also be required. The level of expression of cyclin D1 and SRC (and where necessary ER) may be varied within fairly wide limits, so that the intracellular levels of the two may vary by a wide ratio, for example from 1:10 to 1000:1, preferably 1:1 to 100:1, molar ratio of cyclin D1 to SRC.

While not wishing to be bound by any one theory, the interaction of SRC to both ER and cyclin D1 through similar regions and motifs of SRC suggests that SRC interaction with these components may occur through dimerization of SRC. It may therefore be desirable when performing the invention, particularly in the presence an ER, to ensure sufficient excess of SRC to allow for dimerization to occur. In addition, the dimerization of SRC gives rise to a further novel target for potential modulator compouds, wherein such assays may be conducted as described herein for SRC-cyclin D1 assays, with the D1 component being replace by a second SRC, either identical to or different from the first SRC.

The amount of putative modulator compound which may be added to an assay of the invention will normally be determined by trial and error depending upon the type of compound used. Typically, from about 0.01 to 100 nM concentrations of putative modulator compound may be used, for example from 0.1 to 10 nM. Modulator compounds may be those which either agonise or antagonise the interaction. Antagonists (inhibitors) of the interaction are particularly desirable.

Modulator compounds which may be used may be natural or synthetic chemical compounds used in drug screening programmes. Extracts of plants which contain several characterised or uncharacterised components may also be used. Modulators which are putative inhibitor compounds can be derived from the cyclin D1 and SRC protein sequences. Peptide fragments of from 5 to 40 amino acids, for example from 6 to 10 amino acids from the region of cyclin D1 and SRC which are responsible for the interaction between these proteins may be tested for their ability to disrupt this interaction. Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction between cyclin D1 and SRC.

A particular class of peptide compounds will be those based upon "LXXLL" (SEQ ID NO:6) peptides shown in the accompanying examples. Such peptides are preferably form 5 to 20 amino acids in size, and are of the structure $Z^1$-LXXLL-$Z^2$ (SEQ ID NO:9) where $Z^1$ is an N-terminal or a sequence of from 1 to 8 amino acids, preferably a sequence found immediately N-terminal to a naturally occuring LXXLL (SEQ ID NO:6) motif in an SRC, and $Z^2$ is a terminal or sequence of from 1 to 8 amino acids, preferably a sequence found immediately C-terminal to a naturally occuring LXXLL (SEQ ID NO:6) motif in an SRC or other nuclear receptor interacting protein such as p300 or CBP. $Z^1$ and $Z^2$ may be from the same or different SRC and where from the same, from the same or different motif.

Particular peptides according to this aspect of the invention include those shown in Table 1 below (the peptides are shown in conventional N- to C-terminal order using the standard 1-letter code:

TABLE 1

| | |
|---|---|
| A A S K H K Q L S E L L R S G | SEQ ID NO:1 |
| S H K L V Q L L T T T A E Q | SEQ ID NO:2 |
| E R H K I L H R L L Q E G S | SEQ ID NO:3 |
| K D H Q L L R Y L L D K D E | SEQ ID NO:4 |
| P Q A Q Q K S L Q Q L L T | SEQ ID NO:5 |

In a preferred aspect of the invention, $Z^1$ comprises from 3 to 7 amino acids and contains at least one, such as 1, 2 or 3, residue selected from the group of K and H. In this embodiment of the invention, it is preferred that-the amino acid at position −1, −2 or −3, preferably −2, with respect to the first L of the LXXLL (SEQ ID NO:6) motif is K or H.

Although the second and third amino acids of the LXXLL motif may vary, it is preferred that at least one of said amino acids is charged.

We have also found that peptides of this aspect of the invention are active even where $Z^2$ comprises a single amino acid. Thus, in a preferred aspect of the invention, $z^2$ may be from 1 to 4 amino acids in length.

The abovementioned preferred features may be present separately or in any combination in peptides of the invention.

Peptides comprising an LXXLL (SEQ ID NO:6) motif may comprise multimers of this motif, either in the form of one or more direct repeats, of separated by one or more amino acids. The peptides may also be branched peptide structures, referred to in the art as dendrimers.

Peptide antagonists of the interaction of cyclin D1 with an SRC may be linked, at the C- or N-terminal, to a member of the class of sequences which are membrane translocation sequences capable of directing a polypeptide through the membrane of a eukaryotic cell. Example of such polypeptides include the HSV-1 VP22 protein (Elliot et al, 1997), the HIV Tat protein (for example residues 1–72 or 37–72, Fawell et al, 1994) or a sequence that is derived from the Drosophila melanogaster antennapedia protein. The latter is a peptide containing 16 amino acid residues taken from the third helix of the antennapedia homeodomain protein which translocates across biological membranes (Derossi et al, 1994). This translocation peptide has the sequence: Arg-Gln-Ile-Lys-Ile-Trp-Phe-Gln-Asn-Arg-Arg-Met-Lys-Trp-Lys-Lys (SEQ ID NO:6). The peptide is preferably joined to the N-terminus of polypeptides of the invention which antagonize the interaction of cyclin D1 with an SRC.

Other candidate inhibitor compounds may be based on modelling the 3-dimensional structure of cyclin D1 and SRC and using rational drug design to provide potential inhibitor compounds with particular molecular shape, size and charge characteristics.

Candidate modulator compounds obtained according to the method of the invention may be prepared as a pharmaceutical preparation. Such preparations will comprise the compound together with suitable carriers, diluents and excipients. Such formulations form a further aspect of the present invention. Formulations of inhibitor compounds in particular may be used in methods of treatment of proliferative diseases, particularly those involving cells which grow in response to stimulation by estrogen, for example breast cancer.

Candidate inhibitor compounds may also be used in combination with any other anti-proliferative compounds used to treat hyperproliferative diseases such as cancers. In such a case, the assay of the invention, when conducted in vivo, need not measure the degree of inhibition of binding or transcriptional activation caused by the inhibitor compound being tested. Instead the effect on cell growth or proliferation may be measured. It may be that such a modified assay is run in parallel or subsequent to the main assay of the invention in order to confirm that any effect on cell growth or proliferation is as a result of the inhibition of binding or transcriptional activation caused by said inhibitor compound and not merely a general toxic effect.

A preferred class of other anti-proliferative compounds are anti-estrogens such as tamoxifens, eg. 4-hydroxytamoxifen or pure anti-estrogens such as N-(n-butyl)-11-[3,17beta-dihydroxy-estra-1,3,5(10)-trien-7alpha-yl]N-methylundecanamide, known as ICI 164,384. Such anti-estrogen compounds may be included in the assay in order to determine inhibitor compounds which may act additively or synergistically with anti-estrogens. This will facilitate the provision of combination therapy against estrogen-responsive tumours.

Estrogen responsive tumours are primarily breast tumours although other tumour types which have been found to be estrogen-responsive include endometrial cancer and ovarian carcinoma.

The interaction between cyclin D1 and the SRC may also be used to monitor the status and progress of disease states associated with enhanced transcription of ERE regulated genes. For example, antibodies may be generated which bind to the cyclin/SRC complex or to one or other component in the allosteric form induced by binding to the other. Such antibodies may be raised in routine ways, using as immunogen the cyclin/SRC complex which may be stabilized by using protein cross-linking reagents. The antibodies generated by such an immunogen may be screened against the immunogen and separately against the cyclin and SRC, in order to obtain antibodies which recognise only the proteins when complexed. Such antibodies may be packaged in kits with other suitable reagents for immunodiagnosis and used in the clinic to monitor disease states.

The following Examples illustrate the invention.

Legends to Figures.

FIG. 1. Mapping of the region of cyclin D1 required for ER-mediated transactivation.

(A) The effect of cyclin D1 deletion mutants on ER activation in the presence of ligand. The cyclin D1 derivatives used in this study are shown in the left panel; right side of Figure represents the relative capacity of the mutants to potentiate ERE-dependent transcription. ER-negative COS-7 cells were transfected with expression vectors for wild type ER (200 ng), cyclin D1 or cyclin D1 mutants (2.5 $\mu$g), an internal control §-galactosidase plasmid (0.5 $\mu$g) and an ERE-TATA-luciferase reporter (3 $\mu$g). The effect on ER transactivation of wild type cyclin D1 was set to 100%. These studies were performed in three separate experiments and expressed as mean values with standard deviation less then Ups. The alignment of leucine-rich motif of ER with D-type cyclins are shown on the bottom; the leucine-rich motif in cyclin D1 is indicated as a dark box. The identifiers for the sequences shown are as follows: Cyclin D1 (SEQ ID NO:11), Estrogen receptor (SEQ ID NO:12), the Cyclin D2 (SEQ ID NO:13), and the Cyclin D3 (SEQ ID NO:14).

(B) ER activation by D-type cyclins, cyclin D1 L254/255A point mutant (D1-LALA) and SRC-1 in the presence of ligand. COS-7 cells were transfected with D-type cyclin expression vectors, cyclin D1 Leucine-to-Alanine point mutant (D1-LALA) or SRC-1 expression vector together with wild type ER expression vector, an ERE-TATA-luciferase reporter plasmid and the internal control $\beta$-galactosidase construct. Data are expressed as relative luciferase activity compared with basal ERE-luciferase activity of wild type ER and are normalized for transfection efficiencies.

FIG. 2. Effect of cyclin D1 on helix 12 mutants of ER. The effect of cyclin D1 on ER mutants was tested in COS-7 cells (A, B) and in U2-OS cells (C, D) in the presence of ligand. An ERE-TATA-luciferase reporter construct was used in transient transfections together with cyclin D1 and ER 1-535 (A, C) or ER L543/544A mutants (B, D). $\beta$-Galactosidase served as an internal control. The reporter activity was determined both in the presence (black bars) and in the absence (white bars) of 10 nM 17$\beta$-estradiol. The relative luciferase activity was calculated by normalizing to the b-galactosidase activity. The relative reporter activity of wild type ER in the presence of ligand was used as a reference and set at 100%. In the absence of transfected ER plasmid, cyclin D1 did not induce transcriptional activity of the reporter (data not shown). The transfection were performed in at least five separate experiments and expressed as average ±SD.

FIG. 3. Role of coactivators in cyclin D1—induced transactivation.

(A) Effect of a dominant negative form of SRC-1 (SRC1-DN) on ER transactivation. SRC1-DN encoding amino acids 1245–1441 of SRC-1 (1, 2.5 and 5 $\mu$g) was introduced by transient transfection together with wild type ER (200 ng) and was tested for its ability to modulate ERE-dependent transcription.

(B) Effect of SRCI-DN on SRC-1 and TIF 2 mediated ER transactivation. SRC-1 (3 $\mu$g) or TIF-2 (3 $\mu$g) were transfected with SRC1-DN (3 $\mu$g) and tested for ER transactivation.

(C) Effect of SRC1-DN on cyclin D1-induced transactivation of ER 1–535 mutant. Cyclin D1 was cotransfected with SRC1-DN (1, 2.5, 5 $\mu$g) and tested for its effect on an ER harboring a deletion of coactivator binding site in helix 12 (ER 1-535).

(D) Effect of SRC1-DN on cyclin D1-induced transactivation of ER L543/544A mutant. Cyclin D1 and SRC1-DN (1, 2.5, 5 gg) were transfected and tested for the activity of ER helix 12 point mutant (ER L543/544A). The transient transfections (A-C) were performed in COS-7 cells, which were maintained in DMEM with 10 nM ligand. The relative activity was calculated by normalizing to the internal control and was divided by luciferase activity of ER (mutant) in the presence of ligand. The transfection for each set of conditions were done at least in four independent experiments and expressed as average ±SD.

FIG. 4A. Structure of GST-SRC1 derivatives used to show that amino acids 568 to 782 of SRC-1 are required for cyclin D1 binding.

FIG. 4B. Sequences of peptides P1(SEQ ID NO:15), P2(SEQ ID No:16), P3(SEQ. ID No:17), P4(SEQ ID NO:18), and P4M (SEQ ID NO:19).

FIG. 5. Cyclin D1 mediates ligand-independent recruitment of SRC-1 to ER.
(A) Ligand-independent in vitro binding of SRC-1, ER and cyclin D1. The purified proteins GST-SRC1, His-tagged cyclin D1 and baculovirus-produced ER were tested for in vitro binding-in a GST-pull down assay. GST protein served as negative control. Cyclin D1 and ER were incubated with GST-SRC1 in the presence or absence of 1 $\mu$M 17$\beta$-estradiol and binding was detected by Western blot analysis using anti-cyclin D1 and anti-ER monoclonal antibodies. Lane 1 represents 10%of the input for cyclin D1 and 20% of input of ER proteins.
(B) Cyclin D1 and SRC-1 can interact with DNA-bound ER. Oligonucleotide containing ER binding sequence was biotin 5'-end labeled and bound to paramagnetic particles coated with streptavidin. Purified GST-SRCl, baculovirus produced ER and His-tagged cyclin D1 proteins were tested for DNA binding using these ERE-containing beads and analyzed by Western blotting using antibodies directed against GST, ER and cyclin D1, respectively.

Figure 6A:
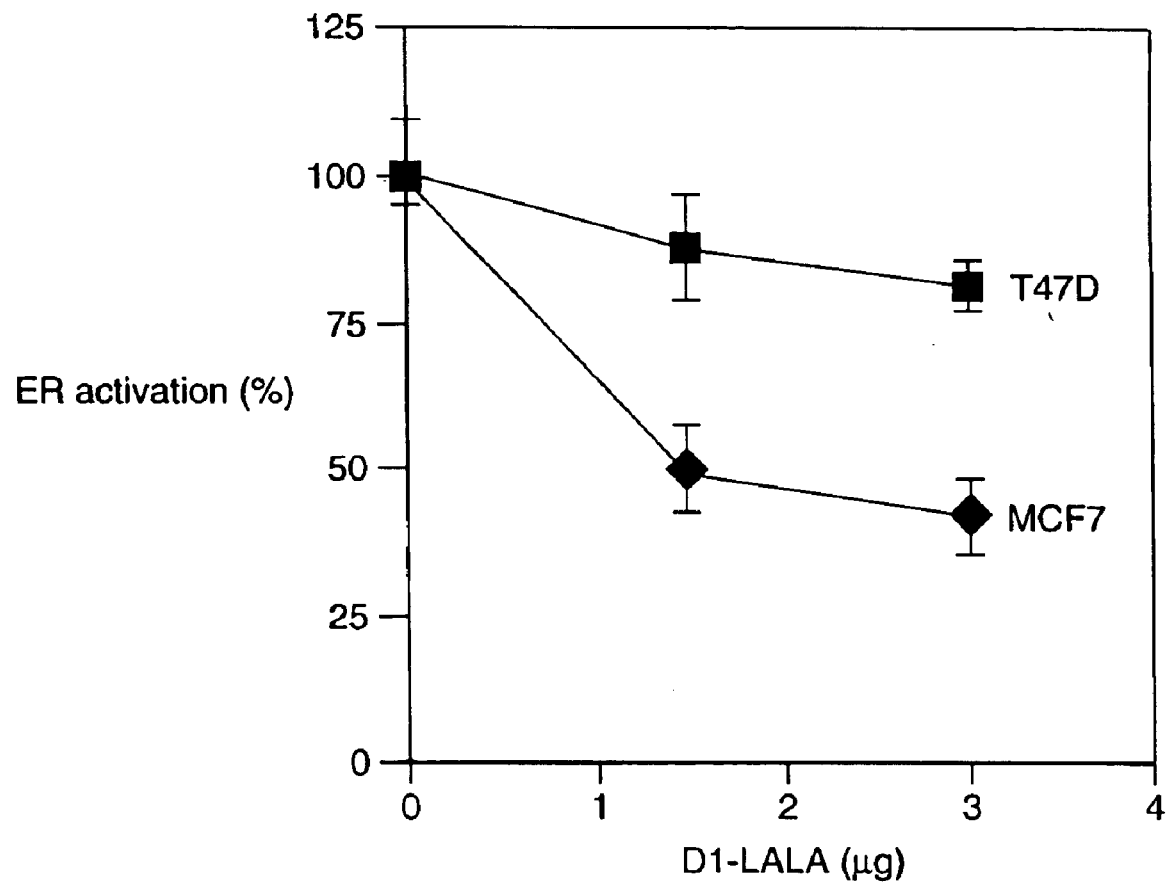
Figure 6B:
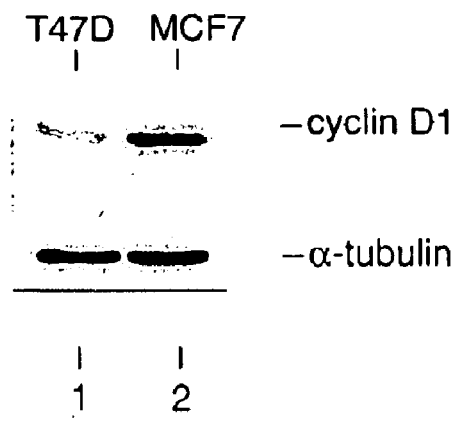

FIG. 6. Role of cyclin D1 in ER transactivation in breast cancer cells.

The ER-containing T47D and MCF-7 breast cancer cells were maintained in 17$\beta$-estradiol enriched medium with 10%fetal calf serum after cotransfection with a cyclin D1 L254/255A mutant expression vector and an ERE-reporter gene for testing its effect on ER activation (left panel). ER transactivation in the absence of co-expression of the cyclin D1 mutant was set at 100%. The right panel shows the expression levels of endogenous cyclin D1 in both breast tumor cell lines.

FIG. 7. Model for cyclin D1-mediated ER transactivation. In the absence of ligand, ER is unable to interact with SRCs directly as its leucine-rich coactivator interaction motif is sterically unavailable for interaction. Ligand-independent binding of cyclin D1 to ER provides a single leucine-rich interaction motif for SRCs which is present in the carboxyl terminus of cyclin D1. This results in partial activation of ER (left panel). Subsequent ligand binding of ER induces a conformational change in ER that also exposes the leucine-rich motif in AF-2 of ER for SRC interaction, allowing higher affinity binding of SRCs to the liganded D1/ER complex (right panel). The observed synergism between estradiol and cyclin D1 in ER activation results from their cooperative recruitment of SRCs to the D1/ER complex. The protein interaction motifs are shown in italics. The identifiers for the depicted motifs are: LXXLL (SEQ ID NO:6) and LLXXXL (SEQ ID NO:20).

The invention is illustrated by the following examples.

The estrogen receptor (ER) belongs to the steroid/nuclear receptor family of ligand-regulated transcription factors. Members of this superfamily display a modular structure with six distinct functional regions (termed A-F), which includes domains for DNA binding, ligand binding and transcriptional activation. Like other members of the nuclear hormone receptor superfamily, ER harbors two transcriptional activation functions (AFs) that act synergistically in transactivation (Kumar et al., 1987; Tzukerman et al., 1994). Transcriptional activation is mediated by means of the autonomous activation function (AF-1) in the N-terminal A/B domain and the ligand-dependent activation function (AF-2) in the C-terminal hormone binding domain (Evans, 1988; Kumar and Chambon, 1988; Beato, 1989). These two regions flank the DNA-binding domain of the receptor. Upon ligand binding, ER binds to estrogen responsive elements, which results in activation of specific ER target genes (Beato, 1989).

It is generally thought that nuclear receptors stimulate transcription through direct binding to several of the basal transcription factors, thereby enhancing the formation of a stable transcription pre-initiation complex (Mitchell and Tjian, 1989). This notion is supported by in vitro protein binding studies which demonstrated that several steroid receptors interact directly with components of the basal transcriptional apparatus, including the TATA-box-binding protein TBP (Sadovsky et al., 1995), TFIIB (Ing et al., 1992; Baniahmad et al., 1993) and human $TAF_{II}30$ (Jacq et al., 1994). However, as described above, several lines of evidence suggest that efficient transactivation requires additional positively acting factors termed coactivators.

Transactivation by steroid/nuclear receptors involves the well-conserved AF-2 domain located in helix 12 of the carboxyl-terminus of the receptors. It has been demonstrated that helix 12 harbors a leucine-rich motif that constitutes a ligand-regulated binding site for coactivators, like SRC-1 (Danielian et al., 1992; Le Douarin et al., 1995; Voegel et al, 1996; vom Baur et al., 1996). Consequently, transactivation by nuclear receptors is dramatically reduced in receptors that contain mutations in helix 12 (Danielian et al., 1992; White et al., 1997). The leucine-rich motif in helix 12 of nuclear receptors is involved in binding to the LXXLL (SEQ ID NO:6) motifs of the steroid receptor coactivators (Le Douarin et al., 1996; Heery et al., 1997).

Recently it was found that, apart from cyclin D1, the steroid receptor coactivator AIB-1 is also frequently amplified in breast cancer (Anzick et al., 1997). In the present work we describe an unexpected relationship between cyclin D1 and steroid receptor coactivators which places cyclin D1 at the center of a complex transcription regulatory network of nuclear hormone receptors and their coactivators. We identify a novel functional domain in cyclin D1 that mediates direct interaction with several of the steroid receptor coactivators.

ER and Cyclin D1 Share a Coactivator Binding Motif.

To study how cyclin D1 activates ER, cyclin D1 deletion mutants were tested for their effect on ER-transactivation. COS-7 cells were transfected with cyclin D1 mutants, together with ER and a luciferase reporter gene construct driven by a minimal TATA promoter linked to an estrogen response element (ERE). FIG. 1A shows that an amino-terminal deletion mutant of cyclin D1 (D1: amino acids 91–295) was still able to activate ER, whereas two carboxyl-terminal deletion mutants of cyclin D1 (D1: amino acids 1–202 and D1: amino acids 1–247) lack ER transactivation capacity. A cyclin D1 mutant lacking the extreme carboxyl-terminus (D1: amino acids 1–267) partially retained ER activation. Together, these data indicate that the domain required for ER activation is located in the carboxyl-terminal 48 amino acids of cyclin D1. This part of the protein is not involved in CDK interaction and is poorly conserved among the different cyclins. Alignment of sequences in this part of cyclin D1 with ER revealed that a motif that resembles the highly conserved leucine-rich coactivator binding motif in AF-2 of ER is present within the domain of cyclin D1 implicated in ER transactivation at the amino acid positions 254–259 (FIG. 1A). This motif is only partially conserved in cyclin D2 and D3, two cyclins that are far less active in ER transactivation (Neuman et al., 1997; Zwijsen et al., 1997). To test the relevance of this leucine-rich domain of cyclin D1 in ER activation, a cyclin D1 mutant was constructed in which leucines 254 and 255 were mutated to alanines (D1 L254/255A). This mutation in cyclin D1 is similar to the mutation in ER (ER L543/544A) that interferes with coactivator binding to AF-2 (Danielian et al., 1992). In contrast to wild type cyclin D1, the L254/255A mutant cyclin D1 was virtually unable to activate wild type ER even though this mutant was equally well expressed and was fully active in other assays (FIG. 1B and see be-low). Cyclins D2 and D3, which lack this leucine-rich motif, behaved similar-to the D1 L254/255A mutant in ER activation (FIG. 1B). These data suggest that cyclin D1 can activate ER through an AF-2-like motif.

Activation of AF-2 Mutant ERs by Cyclin D1.

Figure 2B:
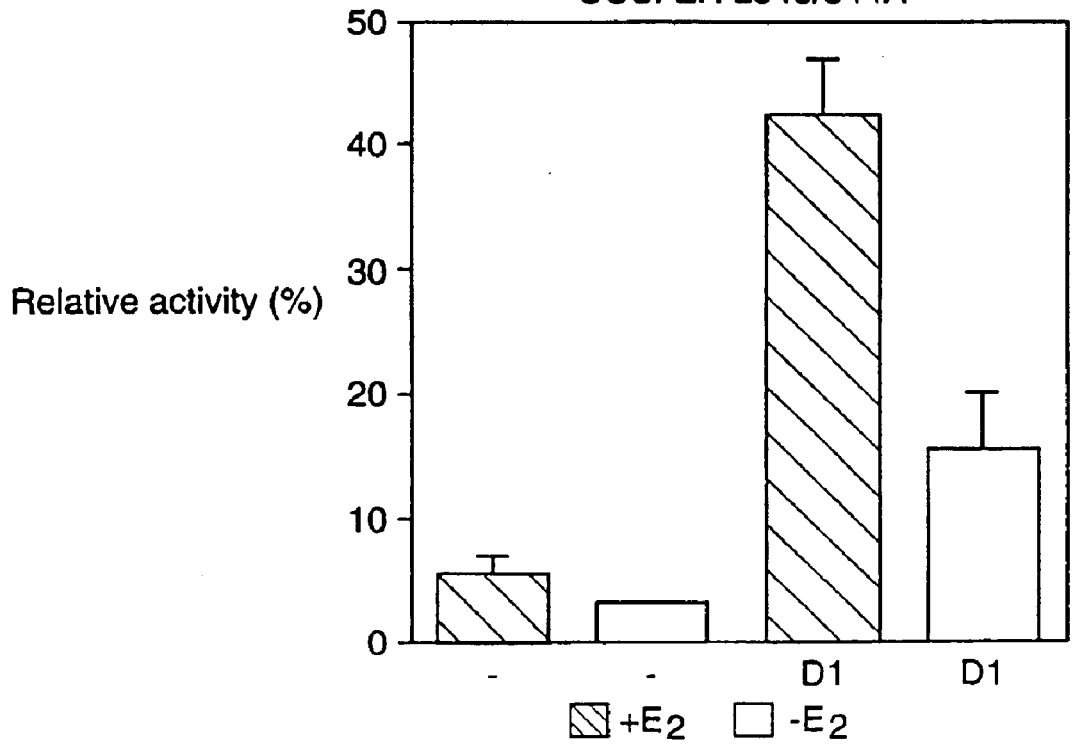
Figure 2C:
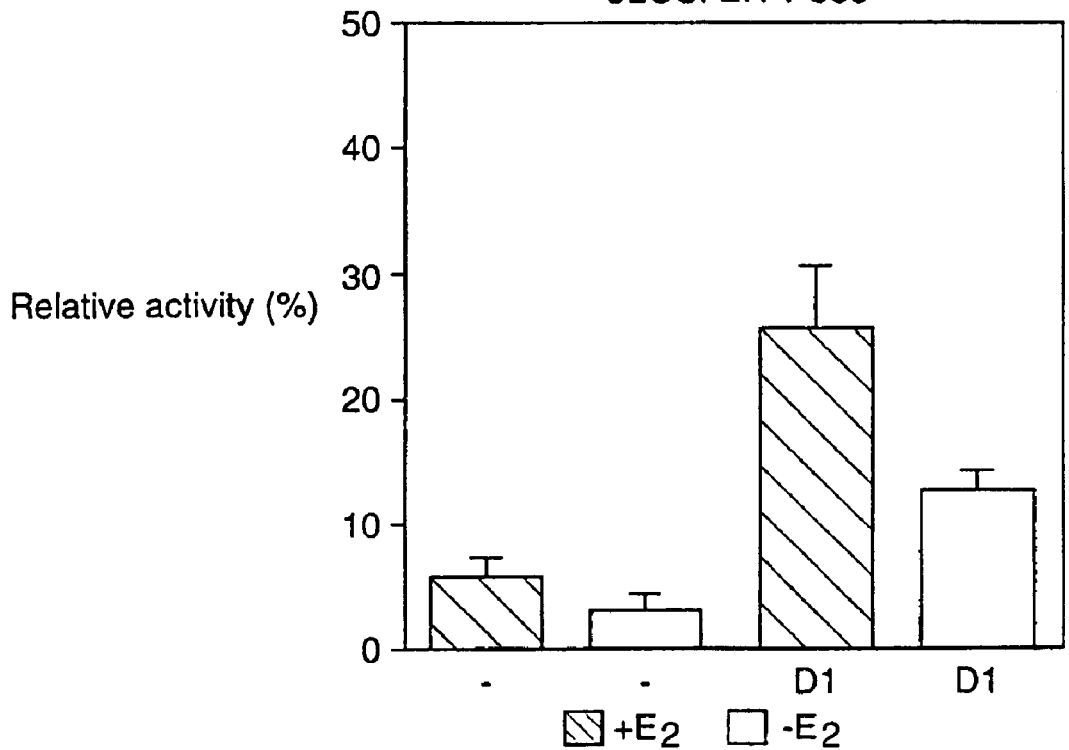
Figure 2D:
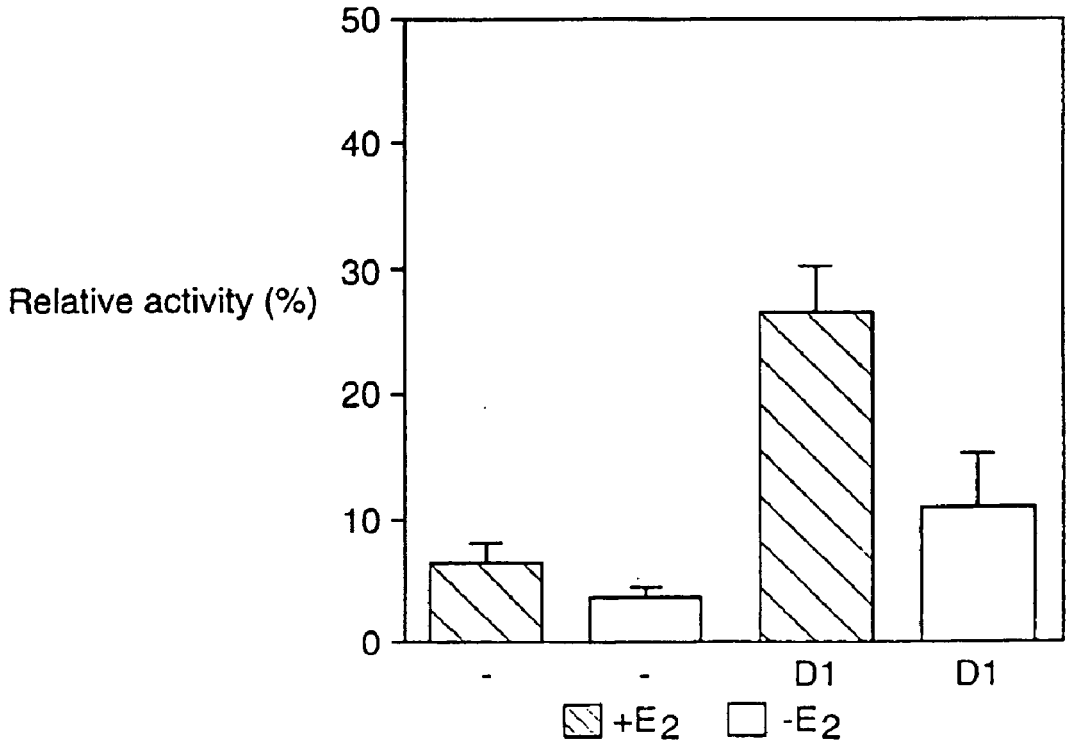

It has been demonstrated that AF-2 mutant ERs are unable to activate transcription, because they cannot recruit steroid receptor coactivators (SRCs) efficiently (Danielian et al., 1992; vom Baur et al., 1996). To determine the role of the AF-2 domain of ER in cyclin D1-mediated transactivation, a deletion mutant and a point mutant in the ligand-regulated carboxyl-terminal activation domain (AF-2) of ER were tested in COS-7 cells. FIG. 2 shows that, as previously reported, the activity of these AF-2 mutant ERs reflects background levels (Danielian et al., 1992; vom Baur et al., 1996). Surprisingly, co-expression of cyclin D1 resulted in a significant activation of the ER AF-2 deletion mutant (ER 1–535) to levels that were up to 40% of ligand-activated wild type receptor (FIG. 2A). Cyclin D1 was also able to induce transcription in the absence of ligand, although this increase was less pronounced. Similarly, ER L543/544A, which harbors a mutation in the leucine-rich coactivator binding site in AF-2 (LLXXXL (SEQ ID NO:20) to AAXXXL (SEQ ID NO:21)), could be activated by cyclin D1 (FIG. 2B). Comparable results were obtained in ER-negative U2-OS osteosarcoma cells (FIGS. 2C, D), indicating that the effect of cyclin D1 is not cell type-specific. These results indicate that cyclin D1 can mediate activation of ER mutants that are unable to interact with SRCs efficiently.

Figure 3A:
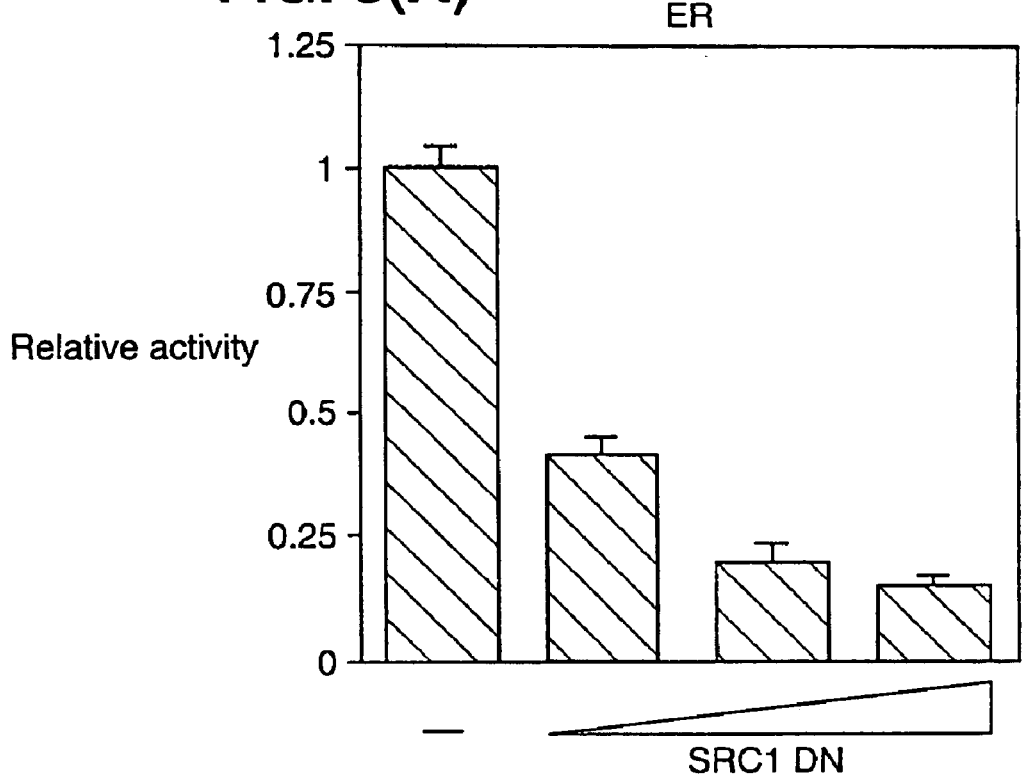
Figure 3B:
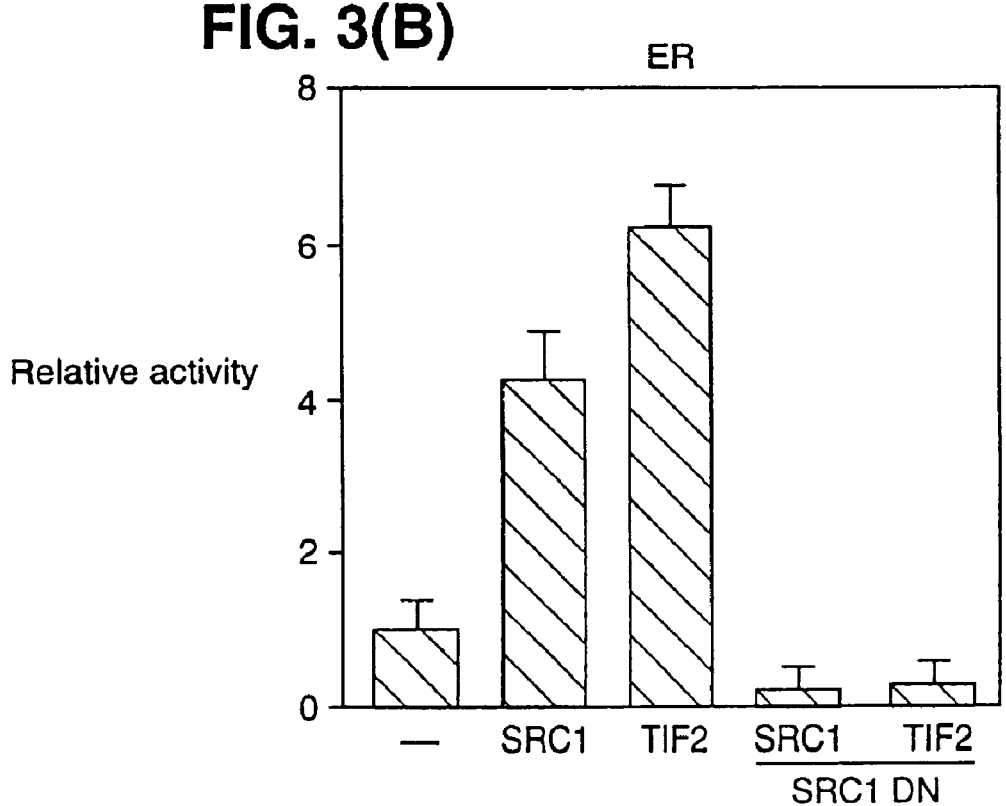
Figure 3C:
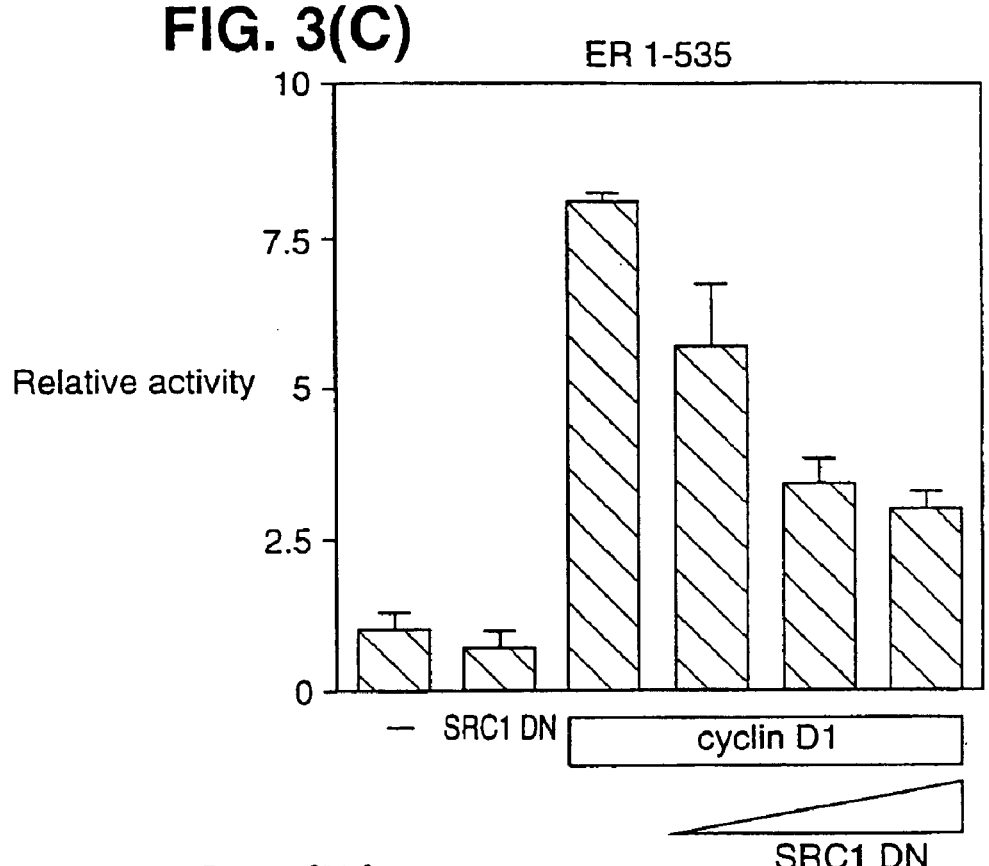
Figure 3D:
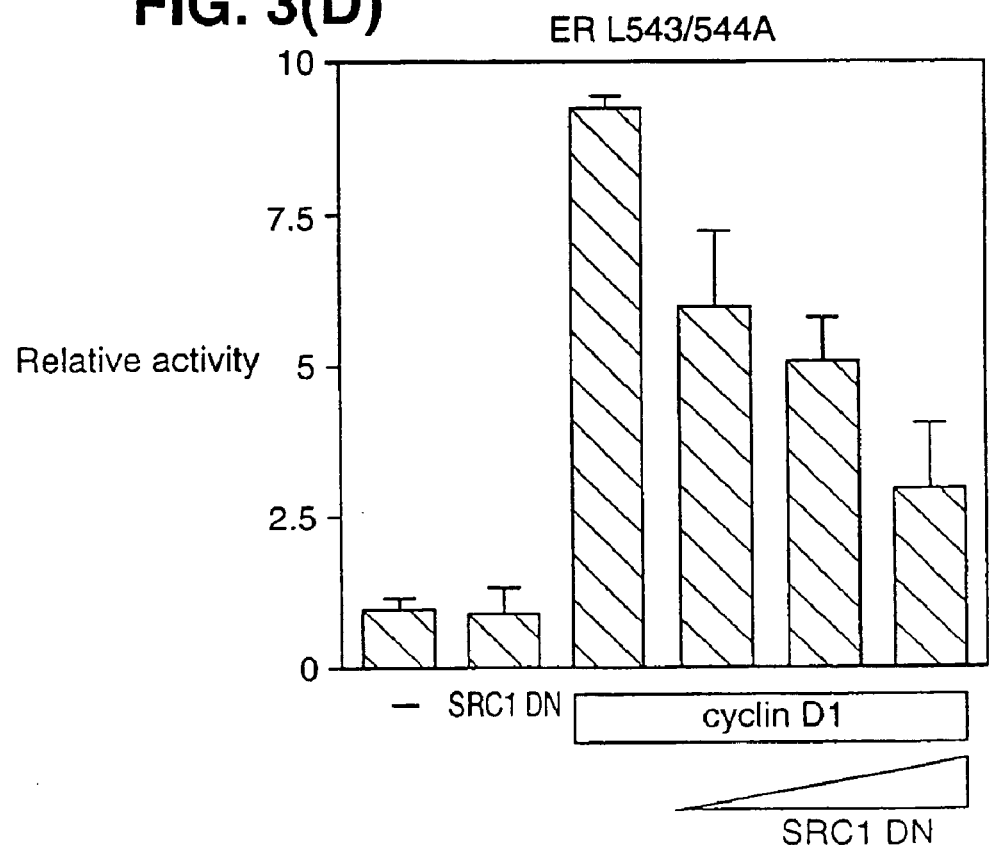

To ask whether SRCs are involved in the cyclin D1-mediated activation of the mutant ERs, a dominant negative mutant of SRC-1 (SRC1-DN, encoding amino acids 1245–1441 of SRC-1) was used. This mutant harbors-a LXXLL (SEQ ID NO:6) motif, which mediates binding to the leucine-rich coactivator binding site in ER (Heery et al., 1997; Le Douarin et al., 1995) but lacks a transactivation domain (Jenster et al., 1997; Spencer et al., 1997). As shown in previous studies (Onate et al., 1995), this construct served as a dominant inhibitor for endogenous SRC-1 function on wild type ER (FIG. 3A). As expected, SRCI-DN inhibited the ability of SRC-1 and of the closely related coactivator TIF2 on ER transactivation (FIG. 3B), whereas it was inactive on the non-related E2F-1 transcription factor (data not shown) Importantly, SRC1-DN markedly repressed the cyclin D1-induced activation of the ER AF-2 mutants (FIGS. 3C, D). These data suggest that the cyclin D1-mediated activation of these mutant ERs somehow requires SRC activity.

Direct Binding of Cyclin D1 to Steroid Receptor Coactivators.

Since the leucine-rich motifs of nuclear receptors have been shown to recruit SRC family coactivators (Danielian et al., 1992; Heery et al., 1997), we tested whether cyclin D1 is also able to interact with SRCs through its leucine-rich motif. COS-7 cells were cotransfected with HA-tagged constructs encoding the nuclear receptor coactivators SRC-1, AIB-1 or p300 (Anzick et al., 1997; Chakravarti et al., 1996; Hanstein et al., 1996; Kamei et al., 1996; Onate et al., 1995) together with control plasmid, plasmids directing the synthesis of wild type cyclin D1 or D1 L254/255A mutant (D1-LALA). 12CA5 HA antibodies were used for immunoprecipitation of whole cell extracts prepared from these cells and co-immunoprecipitation of cyclin D1 (mutants) was examined by Western blot analysis using anti-cyclin D1 antibody. The results showed that wild-type cyclin D1, but not the leucine-to-alanine mutant D1-LALA, co-immunoprecipitates with SRC-1 and AIB-1, whereas binding of both wild type cyclin D1 and D1 LALA mutant to p300 was hardly detectable. Precipitation with the anti-cyclin D1 antibody from the total lysate of the cells transfected with cyclin D1 and cyclin D1-LALA was similar. Binding of cyclin D1 and cyclin D1 L254/255A mutant to ER was then investigated. COS-7 cells were transfected with ER expression vector, cyclin D1 (mutant) and/or control plasmids. Monoclonal ER antibodies were used for immunoprecipitation of ER of whole cell extracts prepared from these cells and co-immunoprecipitation of cyclin D1 (mutant) was examined by Western blot analysis using monoclonal cyclin D1 antibodies. The results show that co-immmunoprecipitation was similar for the (ER and cyclin D1) and (ER and cyclin D1-LALA) samples, showing that the mutant was expressed equally and was unaffected in its ability to bind ER. The activity of cyclin D1 and D1 L254/255A mutant in phosphorylation of pRb in Rb$^{-/-}$ 3T3 cells was also investigated. Cells were transfected with pRb expression vector, cyclin D1 (mutant) and/or control plasmids and were maintained in low serum conditions. After 40 hours, cells were lysed and proteins were separated by low percentage polyacrylamide gel electrophoresis. Differentially phosphorylated species of pRb were detected by Western blotting using the polyclonal pRb antibody (C15, Santa Cruz). Strong bands were seen in the Rb/cyclin D1 and Rb/cyclin D1-LALA bands but not in the control Rb band showing that the mutant was unaffected in its ability to phosphorylate pRb in cells that lack cyclin D1-associated kinase activity.

In summary, these three experiments show that the cyclin D1 mutant L254/255A, which failed to activate ER (FIG. 1B), did not interact with SRC family proteins, though this mutant was expressed equally and was unaffected in its ability to bind ER and to phosphorylate pRb in cells that lack cyclin D1-associated kinase activity. These data suggest that the AF-2-like leucine-rich motif of cyclin D1 mediates binding to SRC-family proteins.

To test whether the interaction between cyclin D1 and SRC-1 is direct, we used bacterially expressed GST-SRC1 and E. coli-produced 6X histidine-tagged cyclin D1 in an in vitro protein binding assay. As described below, His-cyclin D1 strongly binds to GST-SRC1 protein, but not to GST alone, indicating that this association is specific and direct.

To ask which domain or motif of SRC-1 is involved in cyclin D1 binding, we generated a series a GST-SRC1 deletion mutants. The series of GST fusion protein containing SRC-1 (GST-SRC1: 361–1441; GST-SRC1 361–782; GST-SRC1 361–568) or GST-p300(1–595) were tested for direct binding to His-tagged cyclin D1 (His-D1); the GST-SRC1 derivatives are shown in FIG. 4A. The conserved LXXLL (SEQ ID NO:6) motif are boxed and the amino acid boundaries are demonstrated. In the in vitro binding assay, the series of GST-containing proteins were incubated with bacterially expressed His-tagged cyclin D1 and immobilized on glutathione-agarose. Cyclin D1 binding was detected by Western blot analysis using anti-cyclin D1 antibody. Binding was not detected to GST alone. Binding was detected to the GST-SRC1 361–1441, GST-SRC1 361–782 but not to GST-SRC1 361–568 or GST-p300 (1–595) proteins, showing that amino acids 568 to 782 of SRC-1 are required for cyclin D1 binding. Interestingly, this region of SRC-1 harbors three LXXLL (SEQ ID NO:6) motifs, which are involved in binding to nuclear receptors (Heery et al., 1997; Le Douarin et al., 1995; Torchia et al., 1997).

To ask whether the LXXLL (SEQ ID NO:6) motifs of SRC-1 are involved in cyclin D1 binding, a peptide competition experiment was performed. Peptides (0.3 μg and 3 μg) derived from the four LXXLL motifs of SRC1 were used in a GST pull down assay using GST-SRC1 (361–1441) and His-tagged cyclin D1 as described above. The sequence and the position of the peptides in SRC-1 are shown in FIG. 4B. The results of the assay showed that LXXLL (SEQ ID NO:6) peptides, but not a LXXAA mutant peptide, interfered with binding of cyclin D1 to SRC-1. The reduction in binding was greater with 3 μg than with 0.3 μg of each of the LXXLL (SEQ ID NO:6) peptides with no reduction shown with the LXXAA (SEQ ID NO:21)mutant peptide. Of the four SRC-1 LXXLL (SEQ ID NO:6) peptides tested, the P3 peptide, which corresponds to the third of the three centrally located LXXLL motifs, was the best competitor. In another experiment, the ability of peptides to compete with cyclin D1 for binding to GST-SRC1 was investigated. Increasing amounts (100, 200 and 500 nM) of AASKHKQLSELLRSG (SEQ ID NO:1) (LXXLL (SEQ ID NO:6)) and AASKH-KQLSEAARSG (SEQ ID NO:23) (LXXAA) (SEQ ID NO:21) peptides were used in a GST pull down assay using GST-SRC1 (361–1441) and His-tagged cycliin D1. Binding was reduced with increasing concentration of LXXLL (SEQ ID NO:6) peptides but not with increasing concentration of LXXAA (SEQ ID NO:21) peptides. These results indicate that SRC-1 uses the LXXLL (SEQ ID NO:6) motifs not only to interact with nuclear receptors, but also to bind cyclin D1. Since these LXXLL (SEQ ID NO:6) motifs interact with the leucine-rich motifs on nuclear receptors (Heery et al., 1997; Torchia et al., 1997), these data are in good agreement with our experiments described above which suggested a major role for the leucine-rich AF-2-like motif of cyclin D1 in SRC binding. Since both the in vitro and the in vivo association experiments described above were performed in the absence of 17β-estradiol, these data also indicate that the cyclin D1/SRC1 interaction, in contrast to the ER/SRC-1 interaction, is hormone-independent.

Cyclin D1 Act as a Physical Bridge Between ER and SRC-1.

Cyclin D1 activates the estrogen receptor (ER) in a ligand-independent fashion through direct binding to ER (Neuman et al., 1997; Zwijsen et al., 1997). The present study demonstrates that cyclin D1, besides ER, also interacts directly with SRC-1 in vivo and in vitro. These data suggest a model in which cyclin D1 can act as a bridging factor between ER and SRC-1, allowing ligand-independent recruitment of coactivators to ER in the presence of cyclin D1. To test this model directly, we used bacterially expressed 6X histidine-tagged cyclin D1, *E. coli*-produced GST-SRC1 and baculovirus-produced ER in an in vitro GST pull down assay. Protein binding to GST-SRC1 was identified by Western blotting analysis using monoclonal antibodies directed against cyclin D1 and ER. GST protein served as a control for binding specificity. In agreement with several earlier studies, we found that ER binds to GST-SRC1 in a ligand-dependent manner in vitro (Cavailles et al., 1994) (FIG. 5A). Significantly, cyclin D1 could also recruit ER to GST-SRC1 in the absence of ligand (FIG. 5A). These data indicate that cyclin D1 can cause ER activation by acting as a ligand-independent adapter molecule between ER and its coactivator SRC-1.

Figure 5B:
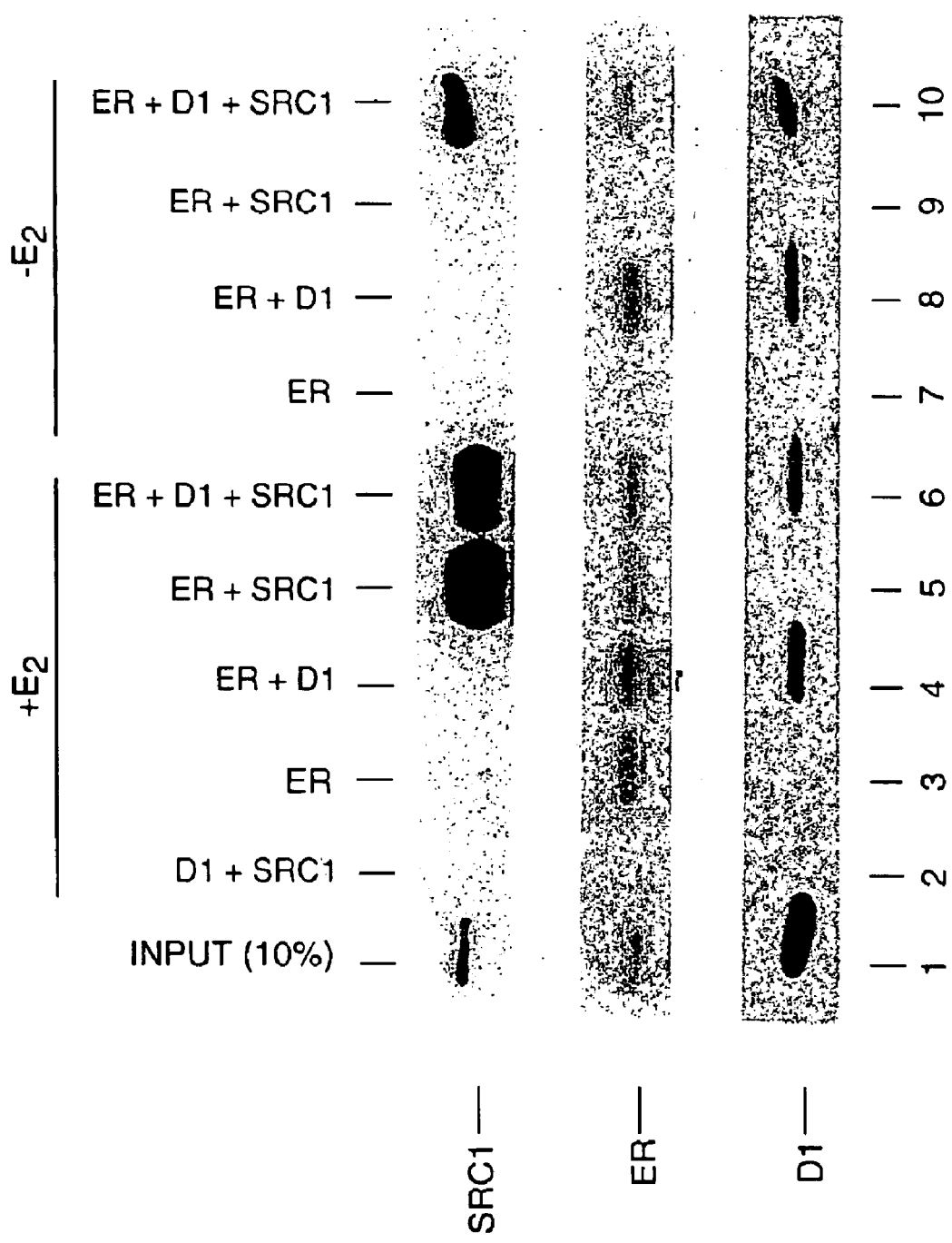

To test whether a ternary complex can also be formed when ER is bound to its cognate DNA binding site (the ERE), we performed a similar ternary complex assay with purified proteins as described above, with the modification that the ternary complex was pulled down with ERE oligonucleotides coupled to paramagnetic beads. FIG. 5B shows that ER binds to ERE in the presence of ligand (lanes 3–6), but also in the absence of ligand when cyclin D1 is present (lanes 8 and 10). Thus, cyclin D1 allows ligand-independent DNA binding of ER to its ERE. More importantly, this assay clearly shows that a ternary complex consisting of ER, cyclin D1 and ER can be formed on DNA both in the presence and in the absence of 17β-estradiol (lanes 6 and 10). These data suggest that cyclin D1 is a bridging factor between ER and SRC-1 also when ER is bound to DNA.

The Role of Cyclin D1 in ER Activation in Breast Cancer.

To get more insight in the role of cyclin D1 in ER transactivation in breast cancers with elevated levels of cyclin D1, we have tested the effect of the mutant cyclin D1 L254/255A on ER activation in two different breast cancer cell lines. This cyclin D1 mutant does bind to ER, but fails both to interact with SRC-1 as shown above and consequently fails to activate ER (FIG. 1B). Therefore, this mutant can act as a dominant negative in cyclin D1-mediated ER transactivation as it binds to ER and fails to recruit coactivators. We tested the effect of this cyclin D1 mutant on ER activation in two breast cancer cell lines, T47D and MCF-7, which contain endogenous wild type ER, but differ in their cyclin D1 protein levels (FIG. 6). In T47D, which contain relative low levels of cyclin D1, co-expression of this cyclin D1 mutant resulted in a slight inhibition of ER activity. In contrast, in MCF-7, which contain relative high levels of cyclin D1 (FIG. 6), the cyclin D1 mutant inhibited up to 50% of ER activity. Thus, this dominant negative cyclin D1 mutant preferentially interferes with ER activation in breast cancer cells that have high levels of cyclin D1 protein. These data strongly support the notion that elevated cyclin D1 protein levels in breast cancer contribute significantly to ER activation.

In parallel experiments, we have used the above dominant negative mutant of cyclin D1 to show that activation of the estrogen receptor complex by D1 stimulates the cell cycle. Cell cycle profiles were analysed using fluuorescence activated cell sorting (FACS)(Allen, 1990; Baldetorp et al, 1998). Transient transfection of MCF-7 breast cancer cells with the L254/255A mutant of cyclin D1 causes an arrest in the cell cycle at the G1/S checkpoint (Table 2), thus confirming the role of the estrogen receptor-cyclin D1 interaction in cell proliferation.

TABLE 2

| Phase of cell cycle | G0/G1 | S | G2/M |
| --- | --- | --- | --- |
| No cyclin D1 | 73.4% | 18.8% | 7.8% |
| Cyclin D1 | 76.5% | 16% | 7.6% |
| Cyclin D1-LALA | 81.9% | 10.2% | 7.9% |

In summary, the invention indicates that cyclin D1 can act as a bridging factor between ER and steroid receptor coactivators (SRCs) which allows the formation of a transcriptionally active ternary complex in the absence of ligand (FIG. 7). It is generally thought that coactivator recruitment by nuclear receptors results from a ligand-induced conformational change in the AF-2 domain of the receptor (Brzozowski et al., 1997; Renaud et al., 1995). Our present data for the first time show an alternative route of coactivator recruitment to ER that can take place in the absence of ligand. As such, these data reveal a novel mechanism of ER activation and establish a direct role for cyclin D1 in regulation of transcription.

Our work has led to the identification of a novel functional domain in the carboxyl terminus of cyclin D1 that mediates direct binding to steroid receptor coactivators like SRC-1 and AIE-1. This leucine-rich motif of cyclin D1 is very similar in character to the ligand-regulated steroid receptor coactivator binding motif that is present in helix 12 of ER and in many other nuclear receptors. Several lines of experimental evidence indicate that the leucine-rich motif of cyclin D1 is required for coactivator recruitment to ER and subsequent activation of ER. First, cyclin D1 interacts directly with SRC-1 both in vivo and in vitro and introduction-of two point mutations in this motif of cyclin D1 abolishes SRC-1 interaction and prevents ER activation by cyclin D1. Second, cyclin D2 and D3 have only a partial conservation of the leucine-rich motif and are hardly active in ER activation (Neuman et al., 1997; Zwijsen et al., 1997). Third, a dominant negative mutant of SRC-1 prevents cyclin D1 activation of ER, indicating that SRCs are required for cycdin D1-mediated activation of ER (FIG. 3). Fourth, in in vitro binding studies cyclin D1 could recruit ER to SRC-1 in the absence of ligand (FIG. 5). Together these data suggest a model in which cyclin D1 can recruit SRCs to ER which results in a transcriptionally productive interaction between ER and its coactivators.

The functional similarity between the leucine-rich motifs of cyclin D1 and ER is also supported by structural analysis. Even though a crystal structure of cyclin D1 is not available at present, the crystal structures of cyclins A and H have been solved (Andersen et al., 1997; Jeffrey et al., 1995). Alignment of the sequence of cyclin D1 with cyclin A and comparison with the structures of cyclins A and H indicates that the leucine-rich motif in the carboxyl terminus of cyclin D1 aligns at the C-terminus of helix 5' of cyclins A and H. Importantly, the PHD program indicates that this part of cyclin D1 has a more than 90% probability to be a-helical and is markedly amphipathic (Rost and Sander, 1993). Since the leucine-rich coactivator binding motif of ER is also an amphipathic helix, it is well-possible that the leucine-rich motifs of cyclin D1 and ER are capable of making similar protein interactions with SRCs.

Consistent with the notion that cyclin D1 and ER have a similar coactivator interaction surface, we found that binding of cyclin D1 to SRC-1 also requires the highly conserved LXXLL motifs in SRC-1. These motifs were recently shown to mediate binding to the leucine-rich coactivator binding site in the amphipathic helix 12 of ER (Heery et al., 1997; Le Douarin et al., 1995; Torchia et al., 1997). Significantly, depending on the pattern of splicing, SRC-1 has three or four LXXLL motifs, three of which are in close proximity (Kalkhoven et al., 1998). In principle, this could allow simultaneous interaction of SRC-1 with the leucine-rich motifs of both ER and cyclin D1. Consistent with this, we observed that a peptide that spans the third LXXLL motif of SRC-1 competed most efficiently the binding between cyclin D1 and SRC-1, whereas previous studies have indicated that the second LXXLL motif of SRC-1 is the preferred site of interaction for ER (Heery et al., 1997; Kalkhoven et al., 1998). Based on these observations we propose that in the absence of ligand, expression of cyclin D1 provides a single interaction site for coactivators on the cyclin D1/ER complex as both binding of cyclin D1 to ER and binding of cyclin D1 to SRC-1 is ligand-independent. This provides a rationale for the ligand-independent activation of ER in the presence of high levels of cyclin D1 (Zwijsen et al., 1997). After ligand binding of ER, the leucine-rich domain in AF-2 is exposed which constitutes a second binding site for SRCs. The presence of two SRC-1 binding sites on the liganded cyclin D1/ER complex provides a rationale for the observed synergism between estradiol and cyclin D1 in ER activation (Zwijsen et al., 1997, FIG. 7).

The model represented in FIG. 7 does not take into account that binding of cyclin D1 to ER also allows ligand-independent DNA binding by ER in vitro and in vivo (FIG. 5B and Zwijsen et al., 1997). Thus, cyclin D1 can not only stimulate coactivator recruitment to ER but also act to enhance DNA binding of ER. Thus, the synergistic action between cyclin D1 and ligand in ER activation may also be due, in part, to synergistic induction of ER DNA binding (FIG. 2 and Zwijsen et al., 1997).

The present study showed that cyclin D1 can bind to SRC-1 and AIB-1, but not to p300. Thus, cyclin D1 can discriminate between the different coactivator families. Apparently, a LXXLL motif (present in both SRCs and p300) is required for cyclin D1 binding, but flanking regions contribute to binding specificity (see also FIG. 4B). The finding that cyclin D1 interacts with at least two members of the SRC family, SRC-1 and AIB-1, would allow in principle for promiscuous activation of steroid receptors by cyclin D1. However, cyclin D1 does not activate the progesterone receptor, nor a number of other steroid hormone receptors (Zwijsen et al., 1997) (R. M. L. Z. and R. B, unpublished data). It is likely that the ability of cyclin D1 to interact with ER directly contributes to the specificity of nuclear receptor activation by cyclin D1.

Cyclin D1 is an important regulator of growth and differentiation of breast epithelium (Fantl et al., 1995; Musgrove et al., 1994; Sicinski et al., 1995; van Diest et al., 1997; Wang et al., 1994; Zwijsen et al., 1996). Significantly, both the genes encoding cyclin D1 and the steroid receptor coactivator AIB-1 are frequently amplified or overexpressed in breast cancer (Anzick et al., 1997; Buckley et al., 1993; Gillett et al., 1994; Schuuring et al., 1992; van Diest et al., 1997). Since the present study indicates that both cyclin D1 and SRCs are components of a multimeric complex involved in ER-mediated transcription, it is conceivable that overexpression of limiting factors in this complex results in deregulation of ER-mediated growth. In agreement with this, we found that a mutant of cyclin D1 that can bind to ER but fails to recruit coactivators acted as a dominant negative mutant for ER activation primarily in breast cancer cells with elevated levels of cyclin D1. Thus, cyclin D1 is likely to contribute significantly to ER activation in breast cancers in which the protein is over-expressed. An important question that we wish to address next is how much of the oncogenic activity of cyclin D1 in breast cancer is mediated through the "classical" cdk4 route and how much through ER activation. The availability of specific mutants of cyclin D1 in which these activities can be separated should allow us to assess the contribution of each of these two activities of cyclin D1 to mammary carcinogenesis separately.

EXPERIMENTAL PROCEDURES

Cell Culture and Transient Transfection Assays.

COS-7 cells and U2-OS cells were maintained in DMEM supplemented with 10% fetal bovine serum. Twenty-four hours before transfection, cells were maintained in DMEM without phenol red containing 5% charcoal-treated FBS. Cells were transfected with 3 µg ERE-TATA-luciferase expression vector, 500 ng β-galactosidase expression vector (internal control);, 200 ng ER expression plasmid and 2.5 µg cyclin D1, coactivators and/or empty vectors as indicated. After sixteen hours, cells were rinsed in PBS and re-fed with fresh medium and ligand (10 nM 17β-estradiol) or vehicle was added. One day later, cells were harvested and assayed for luciferase and β-galactosidase activities. β-galactosidase activity was used to correct for differences in transfection efficiency.

Immunoprecipitation and Western Blotting.

Cells were lysed in ELB containing 250 mM NaCl, 0.1% NP-40, 50 mM HEPES pH 7.0, 5 mM EDTA and protease inhibitors. The cell lysate was pre-cleared three times with 5 μl of normal mouse serum coupled to protein A-Sepharose beads. For immunoprecipitations, the supernatant was incubated with 100 μl of 12CA5 hybridoma supernatant or 10 μl monoclonal antibodyto the estrogenreceptor (TE111.5D11, Neomarkers), which was coupled to protein A sepharose beads at 4° C. After 1 hour, beads were washed in ELE buffer and boiled in Laemmli-buffer. Samples were separated on a 10% SDS/polyacrylamide gel and transferred to nitrocellulose. After blocking with PBS containing 5% milk and 0.1% Tween-20, proteins were detected with monoclonal antibodies directed against cyclin D1 (DCS-6, Neomarkers) and peroxidase-conjugated goat anti-mouse IgG. The blots were washed in PBS containing 0.1% Tween-20 and developed by enhanced chemiluminescence (ECL) reactions (Amersham).

DNA Binding Assay.

For the DNA binding assay we used DNA affinity beads coated with streptavidin (Dynal A/S) and (5-biotin-labeled) DNA oligonucleotides containing a binding sequence for ER as described before (Zwijsen et al., 1997). The complementary DNA strands were annealed in TE buffer containing 100 mM KCl at 75 ûC for 10 min. followed by cooling to room temperature over a period of 2 h. Dynabeads were mixed with biotinylated oligonucleotides in TE buffer containing 1 M NaCl for 15 min., washed and incubated with cell extract in 8 mM Tris-phosphate pH 7.4, 0.12 KCl, 8% glycerol, 4 mM DTT and 0.5% CHAPS for 1 h at 4° C. Subsequently, beads were washed in 20 mM Hepes pH 7.7, 50 mM KCl, 20% glycerol and 0.1% NP-40. The beads were boiled in Laemlli buffer and the proteins were separated on 10% PAGE and identified by Western blotting.

GST Pull Down and Peptide Competition Assay.

GST protein, GST-SRC1 fusion protein and His-tagged cyclin D1 protein were purified as described previously (Zwijsen et al., 1997). Binding between 500 ng GST-SRC1 and 100 ng His-D1 was performed in binding buffer (50 mM NaCl, 50 mM HEPES-KOH pH 7.6, 0.1 mM 0.1% (w/v) NP40, 0.1 mM PMSF and 0.5% charcoal-stripped serum) bound to glutathione-sepharose for 1 hour at 4° C. The beads were washed three times and bound proteins were eluted by boiling for 10 minutes in sample buffer and separated on 10% SDS-PAGE. The binding of His-cyclin D1 to GST-SRC1 was detected by Western blot analysis using monoclonal antibodies directed against cyclin D1 (DCS-6, Neomarkers). For testing a ternary complex, a baculovirus-produced ER (750 ng, Pan Vera) was added to GST-SRC1 (500 ng) and His-D1 (100 ng) in the presence or absence of 1 μM 17β-estradiol using similar conditions as described above. In Western blot analysis monoclonal antibodies directed against cyclin D1 (DCS-6, Neomarkers) and ER (LH2, Novocastra) were used.

For the peptide inhibition assay using the peptides shown in FIG. 4(B), 150 ng GST/GST-SRC1 and 50 ng His-tagged cyclin D1 were used. Peptides were pre-incubated with target protein for 40 minutes at room temperature, prior to addition of the bait. A mixture of GST-fusion peptides, His-tagged cyclin D1 and peptides was incubated for an additional 20 min. at room temperature. The amount of peptides added in competition studies were 0.3 μg and 3 μg. For the peptide inhibition assay using the peptides AASKH-KQLSELLRSG (SEQ ID NO:1)and AASKH-KQLSEAARSG (SEQ ID NO:23) derived from p300 amino acid 74–88, the peptides were pre-incubated with target protein for 20 minutes at room temperature, prior to addition of the bait. The peptides added in competition studies were 100 nM, 200 nM and 500 nM.

The Following Literature Cited Herein is Incorporated by Reference.

Allen (1990) Biopharm Drug Dispos. 11(6) 477–498.
Andersen et al, (1997) Embo J, 16: 958–967.
Anzick et al (1997) Science 277, 965–968.
Baldetorp et al (1998) Cytometry 33(4) 385–393.
Baniahmad et al (1993) Proc Natl Acad Sci USA 90, 8832-8836.
Beato, M. (1989) Cell 56, 335–344.
Beijersbergen, R. L., and Bernards, R. (1996) Biochem. Biophys. Acta, Reviews on Cancer. 1287, 103–120.
Brzozowski et al (1997) Nature, 389: 753–758.
Buckley et al (1993) Oncogene 8, 2127–2133.
Cavailles et al (1994) Proc Natl Acad Sci USA , 91: 10009–10013.
Chakravarti et al (1996) Nature 383, 99–103.
Chen et al (1997) Cell 90, 569–580.
Danielian et al (1992) EMBO J 11, 1025–1033.
Derossi et al (1994) J. Biol. Chem. 269: 10444–10450.
Elliot, G. and O'Hare, P. (1997) Cell 88, 223–233.
Evans, R. M. (1988) Science 240, 889–895.
Fantl et al (1995) Genes Dev 9, 2364–2372.
Fawell, S., et al, (1994) Proc. Natl. Acad. Sci., USA., 91, 664–668.
Fuqua et al (1993) J. Cell Biochem. 51, 135–139.
Gillett et al (1994) Cancer Res, 54: 1812–1817.
Gillett et al (1996) Int. J. Cancer, 69: 92–99.
Hanstein et al (1996) Proc Natl Acad Sci USA 93, 11540–11545.
Heery et al (1997) Nature 387, 733–736.
Hong et al (1997) Mol Cell Biol 17, 2735–2744.
Ing et al (1992) J Biol Chem 267, 17617–17623.
Jacq et al (1994) Cell 79, 107–117.
Jeffrey et al (1995) Nature, 376: 313–320.
Jenster et al (1997) Proc Natl Acad Sci USA 94, 7879–7884.
Kalkhoven et al (1998) EMBO J., 17: 232–243.
Kamei et al (1996) Cell 85, 403–414.
Kumar, V. and Chambon, P. (1988) Cell 55, 145–156.
Kumar et al (1987) Cell 51, 941–951.
Le Douarin et al (1996) EMBO J 15, 6701–6715.
Le Douarin et al (1995) EMBO J. 14, 2020–2033.
Li et al (1997) Proc Natl Acad Sci USA 94, 8479–8484.
McGuire et al. (1991) Mol. Endocrinol. 5, 1571–1577.
Miksicek et al. (1995) Semin. Cancer Biol. 5, 369–379.
Mitchell, P. J., and Tjian, R. (1989) Science 245, 371–388.
Musgrove et al (1994) Proc Natl Acad Sci USA 91, 8022–8026.
Neuman et al (1997) Mol. Cell. Biol. 17, 5338–5347.
Ogata et al (1992) J. Immunol. Methods 148(1–2) i 15–22.
Ogryzko et al (1996) Cell 87, 953–959.
Onate (1995) Science 270, 1354–1357.
Pugh, B. F., and Tjian, R. (1990) Cell 61, 1187–1197.
Renaud et al (1995) Nature, 378: 681–689.
Rost, B., and C. Sander (1993) J Mol Biol, 232: 584–599.
Sadovsky et al (1995) Mol Cell Biol 15, 1554–1563.
Schuuring et al (1992) Oncogene 7, 355–361.
Schuuring et al (1992) Cancer Res, 52: 5229–5234.
Sicinski et al (1995) Cell 82, 621–630.
Smith et al (1996) Proc Natl Acad Sci USA 93, 8884–8888.
Spencer et al (1997) Nature 389, 194–198.
Torchia et al (1997) Nature 387, 677–684.
Tzukerman et al (1994) Mol Endocrinol 8, 21–30.
van Diest et al (1997) Am J Pathol 150, 705–711.
Voegel et al (1996) EMBO J. 15, 3667–3675.

vom Baur et al (1996) EMBO J Z5, 110–124.
Wang et al (1994) Nature 369, 669–671.
White et al (1997) Embo J 16, 1427–1435.

Yao et al (1996) Proc Natl Acad Sci USA 93, 10626–10631.
Zwijsen et al (1996) Mol Cell Biol 16, 2554–2560.
Zwijsen et al (1997) Cell 88, 405–415.

What is claimed is:

1. An isolated peptide of formula:

$Z^1$-LXXLL-$Z^2$ (SEQ ID NO:9)

where at least one X is a charged amino acid;

$Z^1$ comprises from 3 to 7 amino acids and contains at least one residue selected from the group consisting of K and H; and $Z^2$ is a C-terminal or sequence of from 1 to 8 amino acids.

2. A isolated peptide according to claim 1, wherein $Z^1$ and/or $Z^2$ represent a sequence found immediately N-terminal and/or C-terminal respectively to a LXXLL (SEQ ID NO:6) motif in an SRC or other nuclear receptor interacting protein.

3. A isolated peptide consisting of a formula selected from the group.

| | |
|---|---|
| A A S K H K Q L S E L L R S G | (SEQ ID NO:1) |
| S H K L V Q L L T T T A E Q | (SEQ ID NO:2) |
| E R H K I L H R L L Q E G S | (SEQ ID NO:3) |
| K D H Q L L R L L D K D E | (SEQ ID NO:4); | and

| | |
|---|---|
| P Q A Q Q K S L Q Q L L T | (SEQ ID NO:5). |

4. A isolated peptide whose sequence comprises a peptide as defined in claim 1 or 3 joined to a membrane translocation sequence.

5. A composition comprising a isolated peptide according to claim 1 or 3 together with a diluent or carrier.

* * * * *